United States Patent
Alper

(10) Patent No.: US 9,663,567 B2
(45) Date of Patent: May 30, 2017

(54) MONOCLONAL ANTIBODIES AGAINST SEROTRANSFERRIN ANTIGENS, AND USES THEREFOR

(71) Applicant: Alper Biotech LLC, Rockville, MD (US)

(72) Inventor: Özge Alper, Bethesda, MD (US)

(73) Assignee: ALPER BIOTECH LLC, Rockville, MD (US)

( * ) Notice: Subject to any disclaimer, the term of this patent is extended or adjusted under 35 U.S.C. 154(b) by 0 days.

(21) Appl. No.: 14/357,120

(22) PCT Filed: Nov. 9, 2012

(86) PCT No.: PCT/US2012/064476
§ 371 (c)(1),
(2) Date: May 8, 2014

(87) PCT Pub. No.: WO2013/071127
PCT Pub. Date: May 16, 2013

(65) Prior Publication Data
US 2014/0322224 A1     Oct. 30, 2014

Related U.S. Application Data

(60) Provisional application No. 61/557,572, filed on Nov. 9, 2011.

(51) Int. Cl.
*C07K 16/18*     (2006.01)
*G01N 33/574*     (2006.01)
*A61K 49/00*     (2006.01)

(52) U.S. Cl.
CPC .......... *C07K 16/18* (2013.01); *A61K 49/0004* (2013.01); *G01N 33/57407* (2013.01); *G01N 33/57434* (2013.01); *G01N 2333/79* (2013.01)

(58) Field of Classification Search
CPC .............................. C07K 16/18; G01N 33/574
USPC ............. 530/387.9, 391.3, 391.7; 424/139.1; 435/7.1
See application file for complete search history.

(56) References Cited

FOREIGN PATENT DOCUMENTS

WO    WO 2004/070389    *   8/2004           G01N 33/68

* cited by examiner

*Primary Examiner* — Yan Xiao
(74) *Attorney, Agent, or Firm* — Kenealy Vaidya LLP

(57) ABSTRACT

The invention relates to monoclonal antibodies (mAbs) that bind to serotransferrin (TF), hybridoma lines that secrete these antibodies or fragments thereof, and the use of these antibodies to detect TF antigens. Methods and uses for detecting prostate cancer, as well as methods and uses for distinguishing early and late stage prostate cancer are encompassed.

7 Claims, 27 Drawing Sheets

1. TRFE_HUMAN    Mass: 77000    Score: 1312    Matches: 58(41)    Sequences: 23(20)    emPAI: 2.21

Serotransferrin OS=Homo sapiens GN=TF PE=1 SV=2

| Query | Observed | Mr(expt) | Mr(calc) | Delta | Miss | Score | Expect | Rank | Unique | Peptide |
|---|---|---|---|---|---|---|---|---|---|---|
| 4 | 368.2077 | 734.4008 | 734.3963 | 0.0045 | 0 | 44 | 0.0082 | 1 | U | K.GDVAFVK.H |
| 13 | 414.2117 | 826.4088 | 826.3973 | 0.0115 | 0 | 22 | 1.1 | 1 | U | K.HSTIFEK.N |
| 14 | 414.2141 | 826.4136 | 826.3973 | 0.0163 | 0 | (21) | 1.4 | 1 | U | K.HSTIFEK.N |
| 22 | 437.6988 | 873.3830 | 873.4345 | -0.0514 | 0 | (52) | 0.0016 | 1 | U | K.DSAHGFLK.V |
| 23 | 437.7298 | 873.4450 | 873.4345 | 0.0106 | 0 | 58 | 0.0004 | 1 | U | K.DSAHGFLK.V |
| 32 | 483.2838 | 964.5530 | 963.5250 | 1.0280 | 0 | 5 | 61 | 3 | U | R.APNHAVVTR.K |
| 34 | 489.7527 | 977.4908 | 977.4818 | 0.0090 | 0 | 60 | 0.00022 | 1 | U | K.DGAGDVAFVK.H |
| 38 | 500.7382 | 999.4618 | 999.4913 | -0.0294 | 0 | 46 | 0.0048 | 1 | U | K.YLGEEYVK.A |
| 39 | 500.7382 | 999.4618 | 999.4913 | -0.0294 | 0 | (40) | 0.018 | 1 | U | K.YLGEEYVK.A |
| 61 | 583.7908 | 1165.5670 | 1165.5840 | -0.0170 | 0 | 43 | 0.0082 | 1 | U | K.HQTVPQNTGGK.N |
| 68 | 598.2712 | 1194.5278 | 1194.5452 | -0.0173 | 0 | 60 | 0.0016 | 1 | U | K.DSGFQMNQLR.G |
| 69 | 598.2794 | 1194.5442 | 1194.5452 | -0.0009 | 0 | (60) | 0.00017 | 1 | U | K.DSGFQMNQLR.G |

FIG. 2B

| | | | | | | |
|---|---|---|---|---|---|---|
| 74 | 605.2776 | 1210.5406 | 1210.5401 | 0.0006 | (36) | 0.041 a b | K.DSWCENGLR.G + Oxidation (M) |
| 75 | 606.7720 | 1211.5294 | 1210.5401 | 0.9894 | (11) | 12 a b | K.DSWCENGLR.G + Oxidation (M) |
| 76 | 625.2997 | 1248.5848 | 1248.5986 | -0.0138 | 54 | 0.0006 a b | K.SASLWTGNLR.G |
| 79 | 625.2997 | 1248.5848 | 1248.5986 | -0.0138 | (53) | 0.00096 a b | K.SASLWTGNLR.G |
| 86 | 637.3047 | 1272.5948 | 1272.6462 | -0.0514 | 76 | 4.8e-06 a b | K.HTFPNLANK.A |
| 87 | 637.3361 | 1272.6576 | 1272.6462 | 0.0114 | (61) | 0.00014 a b | K.HTFPNLANK.A |
| 88 | 638.8059 | 1275.5972 | 1275.6248 | -0.0276 | (45) | 0.0059 a b | K.EFQLFSSPNGK.D |
| 89 | 638.8059 | 1275.5972 | 1275.6248 | -0.0276 | 52 | 0.0012 a b | K.EFQLFSSPNGK.D |
| 90 | 638.21.87 | 1275.6343 | 1275.6248 | 0.0095 | (28) | 0.28 a b | K.EFQLFSSPNGK.D |
| 91 | 638.8358 | 1275.6570 | 1275.6248 | 0.0323 | (22) | 1.3 a b | K.EFQLFSSPNGK.D |
| 92 | 642.2766 | 1282.5386 | 1282.5618 | -0.0232 | 59 | 0.00019 a b | K.ETIGTGPR.C |
| 93 | 642.2766 | 1282.5386 | 1282.5618 | -0.0232 | (59) | 0.00019 a b | K.ETIGTGPR.C |
| 103 | 662.3289 | 1322.6432 | 1322.6401 | 0.0031 | 63 | 7.7e-05 a b | K.EDSWQHGLR.G |
| 104 | 661.9139 | 1322.7199 | 1322.7095 | 0.0104 | 38 | 0.028 a b | K.DANCHLVFR.M |
| 105 | 661.9177 | 1322.7313 | 1322.7095 | 0.0218 | (36) | 0.05 a b | K.DSAWCHLVFR.M |
| 116 | 689.3552 | 1376.6958 | 1376.6936 | 0.0023 | 95 | 5.9e-08 a b | K.EGAELTENLK.G |
| 119 | 689.8746 | 1377.7346 | 1378.6915 | -0.9568 | (20) | 1.6 a b | K.CLDGAEVAFVK.M + Carbamidomethyl (C) |

FIG. 2C

| | | | | | | | |
|---|---|---|---|---|---|---|---|
| 120 | 460.2557 | 1377.7453 | 1378.6915 | 0.9462 | 1 | 44 | 0.0063 | 1 | U | K.CLLGXMQVAPVK.H + Carbamidomethyl (C) |
| 146 | 739.8638 | 1477.7130 | 1477.7275 | 0.0145 | 0 | (65) | 4.8e-05 | 1 | U | K.MYLGYKYVTAIR.N |
| 147 | 739.8639 | 1477.7132 | 1477.7275 | 0.0143 | 0 | 74 | 6.1e-06 | 1 | U | K.MYLGYKYVTAIR.N |
| 148 | 497.9260 | 1490.7562 | 1490.7518 | 0.0044 | 1 | 68 | 2.7e-05 | 1 | U | K.SKEFQLFSSEMGK.D |
| 149 | 746.3837 | 1490.7648 | 1490.7518 | 0.0131 | 1 | (5) | 55 | 3 | U | K.SKEFQLFSSEMGK.D |
| 151 | 747.8574 | 1493.7002 | 1493.7224 | 0.0222 | 0 | (58) | 0.00027 | 1 | U | K.MYLGYKYVTAIR.N + Oxidation (M) |
| 152 | 747.8574 | 1493.7002 | 1493.7224 | 0.0222 | 0 | (58) | 0.00023 | 1 | U | K.MYLGYKYVTAIR.N + Oxidation (M) |
| 178 | 789.3790 | 1576.7434 | 1576.8072 | 0.0637 | 0 | (55) | 0.00051 | 1 | U | R.TAGNTIPMGLLINK.I |
| 179 | 789.3790 | 1576.7434 | 1576.8072 | 0.0637 | 0 | 55 | 0.00049 | 1 | U | R.TAGNTIPMGLLINK.I |
| 186 | 797.4074 | 1592.8002 | 1592.8021 | 0.0018 | 0 | (45) | 0.0045 | 1 | U | R.TAGNTIPMGLLINK.I + Oxidation (M) |
| 187 | 797.4379 | 1592.8612 | 1592.8021 | 0.0592 | 0 | (32) | 0.088 | 1 | U | R.TAGNTIPMGLLINK.I + Oxidation (M) |
| 199 | 815.3987 | 1628.7828 | 1628.8086 | 0.0258 | 0 | 37 | 0.034 | 1 | U | K.EDFQTPIAVAVVK.K |
| 275 | 658.9875 | 1973.9407 | 1973.9708 | 0.0301 | 1 | 13 | 6.9 | 1 | U | K.EQIVPQYQGKNPDFAR.N |
| 299 | 1079.9968 | 2157.9790 | 2158.0075 | 0.0284 | 0 | 94 | 4.6e-08 | 1 | U | R.IMNGEADAMSLDGGFVTIAGK.C |
| 300 | 720.3419 | 2158.0039 | 2158.0075 | 0.0036 | 0 | (28) | 0.21 | 1 | U | K.IMNGEADAMSLDGGFVTIAGK.C |
| 301 | 1080.0129 | 2158.0112 | 2158.0075 | 0.0038 | 0 | (51) | 0.00097 | 1 | U | K.IMNGEADAMSLDGGFVTIAGK.C |
| 302 | 1080.4921 | 2158.9696 | 2158.0075 | 0.9622 | 0 | (42) | 0.0085 | 1 | U | K.IMNGEADAMSLDGGFVTIAGK.C |

FIG. 2D

| | | | | | | | | |
|---|---|---|---|---|---|---|---|---|
| 303 | 720.6691 | 2158.9855 | 2158.0075 | 0.9780 | 0 | (35) | 0.042 | 1 | U | K.IDNGKIADANSIDGGFVYIAGK.C |
| 307 | 725.6780 | 2174.0122 | 2174.0024 | 0.0098 | 0 | (20) | 1.3 | 1 | D | K.IDNGKIADANSIDGGFVYIAGK.C + Oxidation (M) |
| 308 | 1088.0204 | 2174.0262 | 2174.0024 | 0.0239 | 0 | (8) | 18 | 1 | D | K.IDNGKIADANSIDGGFVYIAGK.C + Oxidation (M) |
| 309 | 1088.0287 | 2174.0428 | 2174.0024 | 0.0405 | 0 | (49) | 0.0017 | 1 | D | K.IDNGKIADANSIDGGFVYIAGK.C + Oxidation (M) |
| 310 | 726.0030 | 2174.9872 | 2174.0024 | 0.9848 | 0 | (10) | 12 | 1 | D | K.IDNGKIADANSIDGGFVYIAGK.C + Oxidation (M) |
| 311 | 1088.5042 | 2174.9938 | 2174.0024 | 0.9915 | 0 | (94) | 5.3e-07 | 1 | D | K.IDNGKIADANSIDGGFVYIAGK.C + Oxidation (M) |
| 316 | 731.0015 | 2189.9827 | 2189.9973 | 0.0146 | 0 | (18) | 2.1 | 1 | D | K.IDNGKIADANSIDGGFVYIAGK.C + 2 Oxidation (M) |
| 317 | 1096.0085 | 2190.0024 | 2189.9973 | 0.0051 | 0 | (81) | 8.6e-07 | 1 | D | K.IDNGKIADANSIDGGFVYIAGK.C + 2 Oxidation (M) |
| 318 | 1096.5042 | 2190.9938 | 2189.9973 | 0.9965 | 0 | (26) | 0.29 | 1 | D | K.IDNGKIADANSIDGGFVYIAGK.C + 2 Oxidation (M) |
| 319 | 731.3400 | 2190.9982 | 2189.9973 | 1.0009 | 0 | (7) | 23 | 1 | D | K.IDNGKIADANSIDGGFVYIAGK.C + 2 Oxidation (M) |
| 361 | 1318.6697 | 3952.9873 | 3953.0098 | 0.0225 | 0 | 83 | 2.8e-07 | 1 | D | R.AIAAMEADAVIDAGLVIDAILAPNHLPVVAKPYGSK. |
| 362 | 1319.0531 | 3954.1375 | 3953.0098 | 1.1277 | 0 | (60) | 5e-05 | 1 | D | R.AIAAMEADAVIDAGLVIDAILANHLPVVAKPYGSK. |

FIG. 2E

| Potential Epitopes | |
|---|---|
| SEQ ID NO: 9 | GDVAFVK |
| SEQ ID NO: 10 | NPDPWAK |
| SEQ ID NO: 11 | NPDPWAK |
| SEQ ID NO: 12 | DSAHGFLK |
| SEQ ID NO: 13 | DSAHGFLK |
| SEQ ID NO: 14 | APNHAVYTR |
| SEQ ID NO: 15 | DXAGDVAFVK |
| SEQ ID NO: 16 | YLPEEYVK |
| SEQ ID NO: 17 | YLQEEYVK |
| SEQ ID NO: 18 | HQTVPQNTGGK |
| SEQ ID NO: 19 | DSGFQMNQLR |
| SEQ ID NO: 20 | DSGFQMNQLR |
| SEQ ID NO: 21 | GDVAFVK |
| SEQ ID NO: 22 | NPDPWAK |
| SEQ ID NO: 23 | NPDPWAK |
| SEQ ID NO: 24 | DSAHGFLK |
| SEQ ID NO: 25 | DSAHGFLK |

FIG. 6

Alper-TF mAb Heavy Chain (SEQ ID NO. 26)

GTTACTCTGAAAGTGTGGCCCTGGGATATTGCAGCCATCACAGACTCTCGGCCTGGCCTGTACTT

TCTCTGGGATTTCACTGAGT ACTTCTGGTATGGGTTTG AGCTGGCTTCGTAAGCCCTCAGGGAAGGCTTT
AGAGTGGCTG GCAAGCATTTGGAATAATGATAATTATTACAACCCATCTTTGAAGAGCC GGCTC
ACAATCTCCAAGGAGACCTCCAACAACCAAGTATTCCTTAAACTCACCAGTGTGGACACTGCAGATTCTA
CCACATACTTCTGTGCTTGG AGAGAGCGGACTATGGTAACTACTTCTATGCTATGGACTACTGGGGTCAA
GGAACCTCAGTCACCGTCTCCTCA

FIG. 7

Alper-TF mAb Heavy Chain (SEQ ID NO. 27)

GACATTCTGATGACCCAGTCTCCAGCTCTCCAGCCTCCTATCTGCATCTGTGGGAGAAATGTCACTATCACATG

T CGAGCAAGTGAAAATATTTACAGTTATTTAGCA TGGTATCAGCAAAAGCAGGAAAATCTCCTCAGCTC

CTACTCTAT AAGGAAAAAACCTTAGCAGAA GGTGTGTCATCAAGGTTCAGTGGCAGTGGATCAGGCACAC

AGTTTCTCTGAGGATCAACAGCCTGCAGCCTGAACAGATTTTGGCAGTTATTACTGT CAACATCATTATGG

TATTCGTGGACGTTCGGTGGAGGCACCAAGCTGGAAATCAAACG

FIG. 8

TF H-Chain

BLASTN 2.2.22 [Sep-27-2009]

Database: migallncseq
Query= 100108-05_A22_CH2-1-T3.ab1 1262 (1262 letters)

Sequences producing significant alignments:

| | Score (bits) | E Value |
|---|---|---|
| 3609.1.84 | 439 | e-125 |
| 3609.13pg.178 | 327 | 5e-91 |
| 3609.4.142 | 325 | 2e-90 |
| 3609.5.147 | 318 | 3e-88 |
| 3609.9.164 | 315 | 3e-87 |
| 3609.12.174 | 315 | 3e-87 |
| CB17H-10 | 311 | 3e-86 |
| 3609.7.153 | 308 | 2e-85 |
| CB17H-3 | 305 | 2e-84 |
| 3609.11.169 | 305 | 2e-84 |

Domain classification requested: Kabat system

| | 100108-05 A22 (H2) | 368 | E P Q S P S P<br>GGAACTCAGTCACGTCTCCTCA | 391 | (SEQ ID NO. 1)<br>(SEQ ID NO. 26) |
|---|---|---|---|---|---|
| 97.3 (289/297) | 3609.1.84 | | ———————————— | | |
| 85.4 (257/301) | 3609.13pg.178 | | ———————————— | | |
| 86.1 (253/294) | 3609.4.142 | | ———————————— | | |
| 100 (14/14) | DSP2.7 | | ———————————— | | |
| 100 (14/14) | DSP2.5 | | ———————————— | | |
| 92.9 (13/14) | DSP2.13 | | ———————————— | | |
| 100 (49/49) | IH4 | 30 | ..C...A.T.... | 53 | |
| 84.6 (33/39) | IH2 | 22 | ..C...A.T...A....... | 45 | |
| 84.4 (254/301) | 3609.5.147 | | ———————————— | | |
| 84.1 (253/301) | 3609.9.164 | | ———————————— | | |
| 84.1 (253/301) | 3609.12.174 | | ———————————— | | |
| 85.6 (244/285) | CB17H-10 | | ———————————— | | |
| 83.4 (251/301) | 3609.7.153 | | ———————————— | | |
| 84.9 (242/285) | CB17H-3 | | ———————————— | | |
| 83.1 (250/301) | 3609.11.169 | | ———————————— | | |

CDR1: T S G M G L (SEQ ID NO. 2)
CDR2: A S I W N D N Y Y N P S L K S (SEQ ID NO. 3)
CDR3: A W R E R T M V T T S M L W T (SEQ ID NO. 4)

FIG. 9G

TF Kappa-Chain

BLASTN 2.2.22 [Sep-27-2009]

Database: migailncseq
Query= 091218-06_A16_OPK-3-T7-Promoter.abi 1282 (1282 letters)

Sequences producing significant alignments:

```
                                            Score      E
                                           (bits)   Value 12-44                                        397   e-112
12-41                                        357   e-100
12-46                                        350    5e-98
12-40                                        338    3e-94
fr12                                         291    3e-80
12-36                                        291    3e-80
fl12                                         269    1e-73
fg12                                         268    4e-73
ci12                                         263    9e-72
12-47                                        255    2e-69
```

Domain classification requested: Kabat system

| GL ID% | IF | | CDR1 | | FWR2 | |
|---|---|---|---|---|---|---|
| | | | R A S E N I Y S Y L A | | W Y Q Q K Q G K S P Q L | |
| | 091218-06_A16 (PK) | T | CGAGCAAGTGAAAATATTTACAGTTATTTAGCA | 94 | TGGTATCAGCAAAAGCAGGAGGAAAATCTCCTCAGCTC | 163 |
| | | | R A S E N I Y S Y L A | | W Y Q Q K Q G K S P Q L | |
| 94.7 (269/284) | 12-44 | . | .............G.................. | 69 | ..........G..A....................... | 138 |
| 90.1 (256/284) | 12-41 | . | .......GG....C..A................ | 69 | ..........G..A....................... | 138 |
| 89.4 (254/284) | 12-46 | . | .............G........A.......... | 69 | ..........G..A....................... | 138 |
| 100 (38/38) | lK1 | | | | | |
| 88.6 (31/35) | lK2 | | | | | |
| 88.0 (250/284) | 12-40 | . | .A...........GG....G............. | 69 | .....T....G..A....................... | 138 |
| 83.5 (237/284) | fr12 | . | .A...........G...A............T.. | 70 | ..........A..CAA.G................C.. | 139 |
| 82.7 (235/284) | 12-38 | . | ......G..C.......TACAG........... | 69 | ..........G..A..G..................... | 138 |
| 81.9 (221/270) | fl12 | . | G............G..GC......G...AAT  | 69 | .........GG..A........................ | 139 |
| 80.7 (230/285) | fgl2 | . | .A...........G...A............T.. | 70 | .....C....A..CAA.G................C.. | 139 |
| 79.6 (226/284) | cil2 | C | .TG......C.G.CC..GGT.CA.GG....... | 69 | ..........G..A..CA.G................. | 138 |
| 80.3 (216/269) | 12-47 | . | AA.......G..A....T..GC......AAT  | 69 | ..........G..A..CA.G..........A...... | 138 |

| | 091218-06 A16 (PRD) | 304 | I P W T F G G G T K L E I K R→<br>TATTCCGTGGACGTTCGGTGGAGGCACCAAGCTGGAAATCAAACG | 348 | (SEQ ID NO. 5)<br>(SEQ ID NO. 27) |
|---|---|---|---|---|---|
| IF | | | T P | | |
| 94.7(269/284) | 12-44 | 279 | ..C.. | 284 | |
| 90.1(256/284) | 12-41 | 279 | ..C.. | 284 | |
| 89.4(254/284) | 12-46 | 279 | ..C.. | 284 | |
| 100(38/38) | JK1 | 1 | ———— | 38 | |
| 88.6(31/35) | JK2 | 4 | ———A... | 38 | |
| 88.0(250/284) | 12-40 | 279 | ..C.. | 284 | |
| 83.5(237/284) | fr12 | 280 | ..C.. | 285 | |
| 82.7(235/284) | 12-38 | 279 | CG... | 284 | |
| 81.9(221/270) | fl12 | | ————A..G..G... | | |
| 80.7(230/285) | fg12 | 280 | G.C.. | 285 | |
| 79.6(226/284) | ca12 | 279 | ..C.. | 284 | |
| 80.3(216/269) | 12-47 | | ———— | | |

CBR1: R A S E N I Y S Y L A (SEQ ID NO. 6)
CBR2: K E K T I L A E (SEQ ID NO. 7)
CBR3: Q H H Y G I P W T (SEQ ID NO. 8)

FIG. 10F

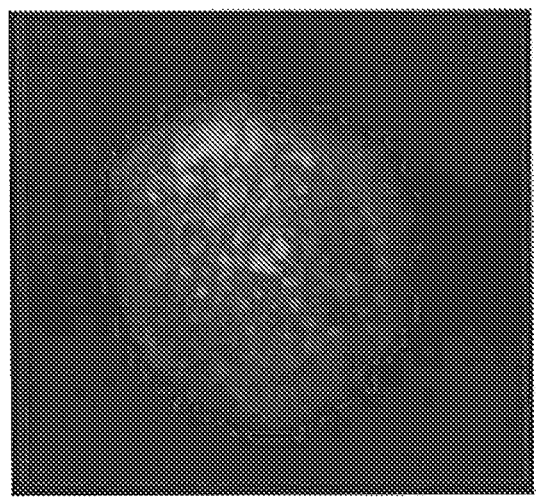
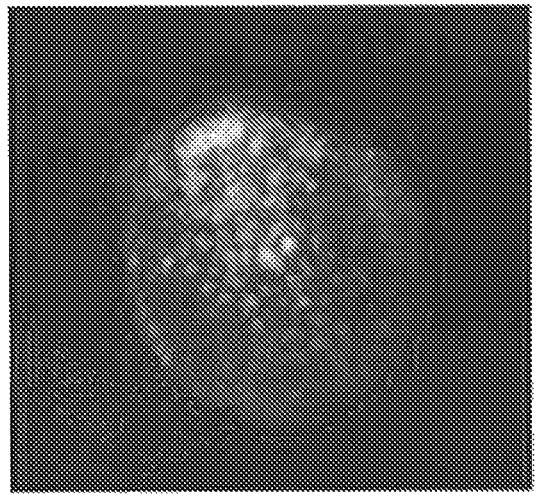
FIG. 11

```
                        SEQUENCE LISTING

<160> NUMBER OF SEQ ID NOS: 84

<210> SEQ ID NO 1
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Val Thr Leu Lys Val Cys Gly Pro Gly Ile Leu Gln Pro Ser Gln Thr
1               5                   10                  15

Leu Gly Leu Ala Cys Thr Phe Ser Gly Ile Ser Leu Ser Thr Ser Gly
            20                  25                  30

Met Gly Leu Ser Trp Leu Arg Lys Pro Ser Gly Lys Ala Leu Glu Trp
        35                  40                  45

Leu Ala Ser Ile Trp Asn Asn Asp Asn Tyr Tyr Asn Pro Ser Leu Lys
    50                  55                  60

Ser Arg Leu Thr Ile Ser Lys Glu Thr Ser Asn Asn Gln Val Phe Leu
65                  70                  75                  80

Lys Leu Thr Ser Val Asp Thr Ala Asp Ser Thr Thr Tyr Phe Cys Ala
                85                  90                  95

Trp Arg Glu Arg Thr Met Val Thr Thr Ser Met Leu Trp Thr Thr Gly
            100                 105                 110

Val Lys Glu Pro Gln Ser Pro Ser Pro
        115                 120

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Thr Ser Gly Met Gly Leu
1               5

<210> SEQ ID NO 3
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3
```

```
Ala Ser Ile Trp Asn Asp Asn Tyr Tyr Asn Pro Ser Leu Lys Ser
1               5                   10                  15

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ala Trp Arg Glu Arg Thr Met Val Thr Thr Ser Met Leu Trp Thr
1               5                   10                  15

<210> SEQ ID NO 5
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Ile Leu Met Thr Gln Ser Pro Ala Ser Leu Ser Ala Ser Val Gly
1               5                   10                  15

Glu Asn Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Leu
            35                  40                  45

Tyr Lys Glu Lys Thr Leu Ala Glu Gly Val Ser Ser Arg Phe Ser Gly
        50                  55                  60

Ser Gly Ser Gly Thr Gln Phe Ser Leu Arg Ile Asn Ser Leu Gln Pro
65                  70                  75                  80

Glu Asp Phe Gly Ser Tyr Tyr Cys Gln His His Tyr Gly Ile Pro Trp
                85                  90                  95

Thr Phe Gly Gly Gly Thr Lys Leu Glu Ile Lys Arg
            100                 105

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Ala Ser Glu Asn Ile Tyr Ser Tyr Leu Ala
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7
```

```
Lys Glu Lys Thr Leu Ala Glu
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln His His Tyr Gly Ile Pro Trp Thr
1               5

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Asp Val Ala Phe Val Lys
1               5

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Pro Asp Pro Trp Ala Lys
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Asn Pro Asp Pro Trp Ala Lys
1               5

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ser Ala His Gly Phe Leu Lys
1               5
```

```
<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asp Ser Ala His Gly Phe Leu Lys
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Pro Asn His Ala Val Val Thr Arg
1               5

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Gly Ala Gly Asp Val Ala Phe Val Lys
1               5                   10

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Tyr Leu Phe Glu Glu Tyr Val Lys
1               5

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Tyr Leu Gly Glu Glu Tyr Val Lys
1               5

<210> SEQ ID NO 18
<211> LENGTH: 11
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 18

His Gln Thr Val Pro Gln Asn Thr Gly Gly Lys
1               5                   10

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Ser Gly Phe Gln Met Asn Gln Leu Arg
1               5                   10

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asp Ser Gly Phe Gln Met Asn Gln Leu Arg
1               5                   10

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Asp Val Ala Phe Val Lys
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asn Pro Asp Pro Trp Ala Lys
1               5

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 23

Asn Pro Asp Pro Trp Ala Lys
1               5

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Ser Ala His Gly Phe Leu Lys
1               5

<210> SEQ ID NO 25
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Ser Ala His Gly Phe Leu Lys
1               5

<210> SEQ ID NO 26
<211> LENGTH: 368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
caggttactc tgaaagtgtg tggccctggg atattgcagc catcacagac tctcggcctg      60
gcctgtactt tctctgggat tcactgagt acttctggta tgggtttgag ctggcttcgt     120 aagcccctcag ggaaggcttt agagtggctg gcaagcattt ggaataatga taattattac    180
aacccatctt tgaagagccg gctcacaatc tccaaggaga cctccaacaa ccaagtattc    240
cttaaactca ccagtgtgga cactgcagat tctaccacat acttctgtgc ttggagagag    300
cggactatgg taactacttc tatgctatgg actactgggg tcaaggaacc tcagtcaccg    360
tctcctca                                                              368

<210> SEQ ID NO 27
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gacattctga tgacccagtc tccagcctcc ctatctgcat ctgtgggaga aaatgtcact     60
atcacatgtc gagcaagtga aaatatttac agttatttag catggtatca gcaaaagcag    120
ggaaaatctc ctcagctcct actctataag gaaaaaacct agcagaagg tgtgtcatca    180

```
aggttcagtg gcagtggatc aggcacacag ttttctctga ggatcaacag cctgcagcct      240
gaagattttg ggagttatta ctgtcaacat cattatggta ttccgtggac gttcggtgga      300
ggcaccaagc tggaaatcaa acg                                              323
```

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Lys Gly Asp Val Ala Phe Val Lys His
1               5

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Lys Asn Pro Asp Pro Trp Ala Lys Asn
1               5

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Lys Asp Ser Ala His Gly Phe Leu Lys Val
1               5                   10

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Arg Ala Pro Asn His Ala Val Val Thr Arg Lys
1               5                   10

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

```
Lys Asp Gly Ala Gly Asp Val Ala Phe Val Lys His
1               5                   10

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Tyr Leu Gly Glu Glu Tyr Val Lys Ala
1               5                   10

<210> SEQ ID NO 34
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Lys His Gln Thr Val Pro Gln Asn Thr Gly Gly Lys Asn
1               5                   10

<210> SEQ ID NO 35
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Lys Asp Ser Gly Phe Gln Met Asn Gln Leu Arg Gly
1               5                   10

<210> SEQ ID NO 36
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Met-Oxidation

<400> SEQUENCE: 36

Lys Asp Ser Gly Phe Gln Met Asn Gln Leu Arg Gly
1               5                   10

<210> SEQ ID NO 37
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37
```

```
Lys Ser Ala Ser Asp Leu Thr Trp Asp Asn Leu Lys Gly
1               5                   10
```

<210> SEQ ID NO 38
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Lys His Ser Thr Ile Phe Glu Asn Leu Ala Asn Lys Ala
1               5                   10
```

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Lys Glu Phe Gln Leu Phe Ser Ser Pro His Gly Lys Asp
1               5                   10
```

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

```
Lys Glu Gly Tyr Tyr Gly Tyr Thr Gly Ala Phe Arg Cys
1               5                   10
```

<210> SEQ ID NO 41
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

```
Lys Lys Asp Ser Gly Phe Gln Met Asn Gln Leu Arg Gly
1               5                   10
```

<210> SEQ ID NO 42
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

```
Lys Asp Ser Ala His Gly Phe Leu Lys Val Pro Pro Arg Met
1               5                   10
```

-continued

```
<210> SEQ ID NO 43
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Lys Lys Ser Ala Ser Asp Leu Thr Trp Asp Asn Leu Lys Gly
1               5                   10

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Cys-Carbamidomethyl

<400> SEQUENCE: 44

Lys Cys Leu Lys Asp Gly Ala Gly Asp Val Ala Phe Val Lys His
1               5                   10                  15

<210> SEQ ID NO 45
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Lys Met Tyr Leu Gly Tyr Glu Tyr Val Thr Ala Ile Arg Asn
1               5                   10

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Lys Ser Lys Glu Phe Gln Leu Phe Ser Ser Pro His Gly Lys Asp
1               5                   10                  15

<210> SEQ ID NO 47
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Met-Oxidation

<400> SEQUENCE: 47
```

```
Lys Met Tyr Leu Gly Tyr Glu Tyr Val Thr Ala Ile Arg Asn
1               5                   10
```

<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

```
Arg Thr Ala Gly Trp Asn Ile Pro Met Gly Leu Leu Tyr Asn Lys Ile
1               5                   10                  15
```

<210> SEQ ID NO 49
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: Met-Oxidation

<400> SEQUENCE: 49

```
Arg Thr Ala Gly Trp Asn Ile Pro Met Gly Leu Leu Tyr Asn Lys Ile
1               5                   10                  15
```

<210> SEQ ID NO 50
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

```
Lys Glu Asp Pro Gln Thr Phe Tyr Tyr Ala Val Ala Val Val Lys Lys
1               5                   10                  15
```

<210> SEQ ID NO 51
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

```
Lys His Gln Thr Val Pro Gln Asn Thr Gly Gly Lys Asn Pro Asp Pro
1               5                   10                  15

Trp Ala Lys Asn
            20
```

<210> SEQ ID NO 52
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 52

Lys Ile Met Asn Gly Glu Ala Asp Ala Met Ser Leu Asp Gly Gly Phe
1               5                   10                  15

Val Tyr Ile Ala Gly Lys Cys
            20

<210> SEQ ID NO 53
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Met-Oxidation

<400> SEQUENCE: 53

Lys Ile Met Asn Gly Glu Ala Asp Ala Met Ser Leu Asp Gly Gly Phe
1               5                   10                  15

Val Tyr Ile Ala Gly Lys Cys
            20

<210> SEQ ID NO 54
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Met-Oxidation
<220> FEATURE:
<221> NAME/KEY: MOD_RES
<222> LOCATION: (10)..(10)
<223> OTHER INFORMATION: Met-Oxidation

<400> SEQUENCE: 54

Lys Ile Met Asn Gly Glu Ala Asp Ala Met Ser Leu Asp Gly Gly Phe
1               5                   10                  15

Val Tyr Ile Ala Gly Lys Cys
            20

<210> SEQ ID NO 55
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Arg Ala Ile Ala Ala Asn Glu Ala Asp Ala Val Thr Leu Asp Ala Gly
1               5                   10                  15

Leu Val Tyr Asp Ala Tyr Leu Ala Pro Asn Asn Leu Lys Pro Val Val
            20                  25                  30

Ala Glu Phe Tyr Gly Ser Lys Glu
        35                  40
```

-continued

<210> SEQ ID NO 56
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Val Thr Leu Lys Val Ser Gly Pro Gly Ile Leu Gln Pro Ser Gln Thr
1               5                  10                  15

Leu Ser Leu Ala Cys Thr Phe Ser Gly Ile Ser Leu Ser Thr Ser Gly
            20                  25                  30

Met Gly Leu Ser Trp Leu Arg Lys Pro Ser Gly Lys Ala Leu Glu Trp
        35                  40                  45

Leu Ala Ser Ile Trp Asn Asn Asp Asn Tyr Tyr Asn Pro Ser Leu Lys
    50                  55                  60

Ser Arg Leu Thr Ile Ser Lys Glu Thr Ser Asn Tyr Gln Val Phe Leu
65                  70                  75                  80

Lys Leu Thr Ser Val Asp Thr Ala Asp Ser Ala Thr Tyr Tyr Gly Ala
                85                  90                  95

Trp Arg Glu
```

<210> SEQ ID NO 57
<211> LENGTH: 297
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
gttactctga aagtgtctgg ccctgggata ttgcagccat cacagactct cagcctggcc      60
tgtactttct ctgggatttc actgagtact tctggtatgg gtttgagctg gcttcgtaag     120
ccctcaggga aggctttaga gtggctggca agcatttgga ataatgataa ctactacaac     180
ccatctttga gagccggct cacaatctcc aaggagacct ccaactacca agtattcctt     240
aaactcacca gtgtggacac tgcagattct gccacatact acggtgcttg agagag        297
```

<210> SEQ ID NO 58
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
caggttactc tgaaagagtc tggccctggt atattgcagc cctcccagac cctcagtctg      60
acctgttctt tctctgggtt ttcactgagc acttttggta tgggtgtgag ctggattcgt     120
cagccttcag ggaagggtct ggagtggctg gcacacattt attgggatga tgacaagcac     180
tataacccat ccttgaagag ccggctcaca atctccaagg atacctccaa caaccaggta     240
ttcctcaaga tcaccactgt ggacactgca gatactgcca catactactg tgctcgaaga     300
g                                                                     301
```

<210> SEQ ID NO 59

```
<211> LENGTH: 294
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
caggttactc tgaaagagtc tggccctggg atattgcagc cctcccagac cctcagtctg      60
acttgttctt tctctgggtt ttcactgagc acttctaata tgggtatagg ctggattcgt     120
cagccttcag ggaagggtct agagtggctg gcacacattt ggtggaatga tgataagtac     180
tataacccat ccctgaagag ccggctcaca atctccaagg atacctccaa caaccaggta     240
ttcctcaaga tcaccagtgt ggacactgca gatactgcca catactactg tgct           294

<210> SEQ ID NO 60
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
actatggtaa ctac                                                        14

<210> SEQ ID NO 61
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
actatggtaa ctac                                                        14

<210> SEQ ID NO 62
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
actatggtga ctac                                                        14

<210> SEQ ID NO 63
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
ctatgctatg gactactggg gtcaaggaac ctcagtcacc gtctcctca                  49

<210> SEQ ID NO 64
<211> LENGTH: 39
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gactactggg gccaaggcac cactctcaca gtctcctca                             39

<210> SEQ ID NO 65
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
caggttactc tgaaagagtc tggccctggt atattgcagc cctcgcagac cctcagtctg      60
acttgttctt tctctgggtt ttcactgagt acttttggta tgggtgtgag ctggattcgt     120
cagccttcag ggaaggatct ggagtggctg gcacacattt attgggatga tgacaagcac     180
tataacccat ccttgaagag ccagctcaga atctccaagg atacctccaa caaccaggta     240
ttcctcaaga tcaccactgt ggacactgta gatactgcca catactactg tgctcgaaga     300
g                                                                    301

<210> SEQ ID NO 66
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
caggttactc tgaaagagtc tggccctggt atattgcagc cctcccagac cctcagtctg      60
acttgttctt tctctgtgtt ttcactgagc acttttggta tgggtgtgag ctggattcgt     120
cagccttcag ggaagggtct ggagtggctg gcacacattt attgggatga ggacaagcac     180
tataaaccat ccttgaagag ccggctcaca atctccaagg atacctccaa caaccaggta     240
ttcctcaaga tcaccactgt ggacactgca gatactgcca catactactc tgctcgaaga     300
g                                                                    301

<210> SEQ ID NO 67
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
caggttactc tgaaagagtc tggccctggg atattgcagt cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacccat ccctgaagag ccggctcaca atctccaagg atacctccag aaaccaggta     240
```
ttcctcaaga tcaccagtgt ggacactgca gatactgcca catactactg tgctcgaaga    300
g                                                                    301

<210> SEQ ID NO 68
<211> LENGTH: 285
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
caggttactc tgaaagagtc tggccctggg atattgcagc cctcccagac cctcagtctg     60
acttgttctt tctctgggtt ttcactgagc acttctaata tgggtatagg ctggattcgt    120
cagccttcag ggaagggtct agagtggctg gcacacattt ggtggaatga tgataagtac    180
tataacccat ccctgaagag ccggctcaca atctccaagg atacctccaa caaccaggta    240
ttcctcaaga tcaccactgt ggacactgca gatactgcca catac                    285

<210> SEQ ID NO 69
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
caggttactc tgaaagagtc tggccctggg atattgcagc cctcccagac cctcagtctg     60
acttgttctt tctctgggtt ttcactgagc acttttggta tgggtgtagg ctggattcgt    120
cagccttcag ggaagggtct ggagtggctg gcacacattt ggtgggatga tgataagtac    180
tataacccag ccctgaagag tcggctcaca atctccaagg atacctccaa aaaccaggta    240
ttcctcaaga tcgccaatgt ggacactgca gatactgcca catactactg tgctcgaata    300
g                                                                    301

<210> SEQ ID NO 70
<211> LENGTH: 285
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
caggttactc tgaaagagtc tggccctggt atattgcagc cctcccagac cctcagtctg     60
acttgttctt tctctgggtt ttcactgagc acttttggta tgggtatagg ctggattcgt    120
cagccttcag ggaagggtct agagtggctg gcacacattt ggtgggatga tgataagtac    180
tataacccag ccctgaagag tcggctcaca atctccaagg atacctccaa caaccaggta    240
ttcctcaaga tcaccagtgt ggacactgca gatactgcca catac                    285

<210> SEQ ID NO 71
<211> LENGTH: 301
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
cagattactc agaaagagtc tggccctggg atattgcagc cctcccagac cctcagtctg     60
acttgttctt tctctgggtt ttcactgagc acttctggta tgggtgtagg ctggattcat    120
cagccttcag ggaatggtct ggagtggctg gcacacattt ggtggaatga taataagtac    180
tataacacag ccctgaagag ccggctcaca atctccaagg atacctccaa caaccaggta    240
ttcctcaaga tcgccagtgt ggacactgca gatactgcca catactactg tgctcgaata    300
g                                                                    301

<210> SEQ ID NO 72
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro
                85                  90                  95

<210> SEQ ID NO 73
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
gacatccaga tgactcagtc tccagcctcc ctatctgcat ctgtgggaga aactgtcacc     60
atcacatgtc gagcaagtga gaatatttac agttatttag catggtatca gcagaaacag    120
ggaaaatctc ctcagctcct ggtctataat gcaaaaacct tagcagaagg tgtgccatca    180
aggttcagtg gcagtggatc aggcacacag ttttctctga agatcaacag cctgcagcct    240
gaagattttg ggagttatta ctgtcaacat cattatggta ctcc                     284

<210> SEQ ID NO 74
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

```
<400> SEQUENCE: 74
gacatccaga tgactcagtc tccagcctcc ctatctgcat ctgtgggaga aactgtcacc      60
atcacatgtc gagcaagtgg gaatattcac aattatttag catggtatca gcagaaacag     120
ggaaaatctc ctcagctcct ggtctataat gcaaaaacct tagcagatgg tgtgccatca     180
aggttcagtg gcagtggatc aggaacacaa tattctctca agatcaacag cctgcagcct     240
gaagattttg ggagttatta ctgtcaacat ttttggagta ctcc                      284

<210> SEQ ID NO 75
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gacatccaga tgactcagtc tccagcctcc ctatctgtat ctgtgggaga aactgtcacc      60
atcacatgtc gagcaagtga gaatatttac agtaatttag catggtatca gcagaaacag     120
ggaaaatctc ctcagctcct ggtctatgct gcaacaaact tagcagatgg tgtgccatca     180
aggttcagtg gcagtggatc aggcacacag tattccctca agatcaacag cctgcagtct     240
gaagattttg ggagttatta ctgtcaacat ttttgggggta ctcc                     284

<210> SEQ ID NO 76
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
tggacgttcg gtggaggcac caagctggaa atcaaacg                              38

<210> SEQ ID NO 77
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
acgttcggag gggggaccaa gctggaaata aaacg                                 35

<210> SEQ ID NO 78
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gacattcaga tgactcagtc tccagcctcc ctatctgcat ctgtgggaga aactgtcacc      60
atcacatgtc aagcaagtga gaatattgcc agtgatttag catggtatta gcagaaacag     120
ggaaaatctc ctcagctcct ggtctatgat gcgagaaact tagcagatgg tgtgccatca     180
```

```
aggttcagtg gcagtggatc aggcacacac tattctctca atatccacag cctgcagtct    240
gaagatgttg cgagatatta ctgtcaacat tattatggta ctcc                     284
```

<210> SEQ ID NO 79
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79

```
acatccagat gactcagtct ccagcctcct ctttctgcat ctctgggaga aagtgtcacc    60
atcacatgtc aagcaagtga gaatattgac aattatttat catggtatca gcaaaaacca   120
aggaaatctc ctcagcccct gatcaattat acaaccaact ttgcagatgg ggttccatca   180
gggtctagtg gcagtggatc aggcacacag ttttctctca agatcaacag cctgcaacca   240
gaagatgttg caagtcatta ctgtcaacat cattatagta ctcc                     284
```

<210> SEQ ID NO 80
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80

```
gacatccaga tgactcagtc tccagcctcc ctggctgcat ctgtgggaga aactgtcacc    60
atcacatgtc gagcaagtga gaacatttac tacagtttag catggtatca gcagaagcaa   120
gggaaatctc ctcagctcct gatctataat gcaaacagct tggaagatgg tgtcccatcg   180
aggttcagtg gcagtggatc tgggacacag tattctatga gatcaacag catgcagcct    240 gaagataccg caacttattt ctgtaaacag gcttatgacg ttcc                     284
```

<210> SEQ ID NO 81
<211> LENGTH: 270
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81

```
gacatccaga tgactcagtc tccagcttca ctgtctgcat ctgtgggaga aactgtcacc    60
atcacatgtg gagcaagtga gaatatttac ggtgctttaa attggtatca gcggaaacag   120
ggaaaatctc ctcagctcct gatctatggt gcaaccaact ggcagatgg catgtcatcg    180 aggttcagtg gcagtggatc tggtagacag tattctctca agatcagtag cctgcatcct    240
gacgatgttg caacgtatta ctgtcaaaat                                     270
```

<210> SEQ ID NO 82
<211> LENGTH: 285
<212> TYPE: DNA
<213> ORGANISM: Artificial Sequence
<220> FEATURE:
<221> NAME/KEY: source
<223> OTHER INFORMATION: /note="Description of Artificial Sequence:

```
          Synthetic polynucleotide"

<400> SEQUENCE: 82
gacatccaga tgactcagtg tccagccacc cctttctgca tctctggaag aaagtgtcac       60
catcacatgt caagcaagtg agaatattga caattattta tcatggtctc agcaaaaacc      120
aaggaaatct cctcagcccc tgatcaatta tacgaccagc ttggcagatg gggttccatc      180
aaggtctagt ggcagtggat caggcacaca gttttctctc aagatcaaca acttgcaaac      240
agaagatgtt gcaagttact actgtcaaca tcattattgg actcc                      285

<210> SEQ ID NO 83
<211> LENGTH: 284
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
gacattcaga tgacccagtc tcctgcctcc cagtctgcat ctctgggaga aagtgtcacc       60
atcacatgcc tggcaagtca gaccattggt acatggttag catggtatca gcagaaacca      120
gggaaatctc ctcagctcct gatttatgct gcaaccagct tggcagatgg ggtcccatca      180
aggttcagtg gtagtggatc tggcacaaaa ttttctttca agatcagcag cctacaggct      240
gaagattttg taagttatta ctgtcaacaa ctttacagta ctcc                       284

<210> SEQ ID NO 84
<211> LENGTH: 269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
gacatccagg tgactcagtc tccagcgtcc ctgtctgcac ctgtgggaga aagtgtctcc       60
atcacatgta aagcaagtga agaaatttat agtgctttaa attggtatca gcagaaacca      120
gggaaatctc cacagctcct gatctattat gcaaccagct tgggagatga tgtgccctca      180
aggttcagtg gcagtaaatc tggcacacag tattccctca agatcagcag cctgcagcct      240
gaagatcttg caacttatta ctgtgaaca                                        269
```

MONOCLONAL ANTIBODIES AGAINST SEROTRANSFERRIN ANTIGENS, AND USES THEREFOR

This application is a National Stage Entry of International Application No. PCT/US2012/064476, filed on Nov. 9, 2012, which claims priority to U.S. application Ser. No. 61/557,572 filed on Nov. 9, 2011, each of which is incorporated herein by reference in its entirety.

The invention generally relates to monoclonal antibodies (mAbs) or antigen binding fragments thereof that bind serotransferrin (TF), to hybridoma lines that secrete the antibodies or antigen binding fragments, to pharmaceutical compositions comprising the antibodies and antigen binding fragments, and to the use of antibodies, antibody fragments, and pharmaceutical compositions for the detection of TF, and for the diagnosis of cancer.

Serotransferrin (TF) is a glycoprotein with an approximate molecular weight of 76,500 Daltons (76.5 kDa). The function of TF is to transport iron from the intestine, reticuloendothelial system, and liver parenchymal cells to all proliferating cells in the body, TF may also have a physiologic role as granulocyte/pollen-binding protein (GPBP) involved in the removal of certain organic matter and allergens from serum, and may have a further role in stimulating cell proliferation, Human TF is described in the database UniProtKB/Swiss-Prot TRFE_HUMAN, P02787-1.

As advances in proteomic biotechnology have been made, many researchers interested in detection of a variety of disease states, including cancer, have turned their focus to identification of potential biomarkers of such disease states. Biomarkers are molecules that allow for the detection and/or isolation of a particular cell type and are specific for a disease state. For example, in prostate cancer, prostate-specific antigen (PSA) is a known biomarker. PSA is known to be present in small quantities in the serum of men with healthy prostates and is often elevated in the serum of men with prostate cancer. In the United States, the US, Food and Drug Administration has approved the PSA test for annual screening of prostate cancer in men 50 years and older. However, a 2012 review commissioned by the U.S. Preventative Services Task Force concluded that PSA-based screening results in a small or no reduction in prostate cancer-specific mortality. Moreover, frequent over diagnosis of prostate cancer is associated with the PSA test, resulting in anxiety for receiving false positives, biopsy pain, and other complications from biopsy. Similar issues with biomarker screening have been associated with other cancers, such as the CA-125 test for ovarian cancer. For these reasons, there remains a need to identify new cancer biomarkers that more accurately diagnose patients suffering from particular types of cancer.

Prior studies comparing gene expression in tissue samples with that of cancer cell lines have indicated that TF expression is lower in cancer cells. For example, the publicly available GeneNote data for TF indicates that, when compared using commercially-available first-generation RNA microarrays, TF mRNA expression was lower in a number of cancer cell lines compared to cells derived from normal healthy human tissue, including thymus, bone marrow, brain, heart, kidney, lung, skin, salivary gland, and prostate. Specifically, for prostate, TF mRNA expression was at least 7-fold greater in normal human prostate tissue than in ALVA31 prostate cancer cells, See GeneCard for TF Gene, available at http://www.genecards.org/cgi-bin/carddisp.pl?geneTF&search=transferrin. Because mRNA expression ordinarily correlates with protein expression, one having ordinary skill in the art would not have suspected that TF protein might serve as a biomarker for these cancers, especially in thymus, bone marrow, brain, heart, kidney, lung, skin, salivary gland, and prostate cancer.

The invention is based in part on the discovery that a monoclonal antibody specific for TF (herein referred to as "anti-TF mAb" or "Alper-TF mAb") can detect TF tissue, cells, whole blood, serum, plasma, and urine from healthy and cancerous patients. The inventor's experiments with Alper-TF mAb unexpectedly demonstrate that TF protein expression is elevated in patients with cancer. Moreover, Alper-TF mAb can be utilized in immunocytochemical assays, including but not limited to immunohistochemical or immunofluorescence assays, to determine the localization of TF, and to determine the severity or stage of cancer depending on its localization and/or expression level. Using the novel antibody of the present invention, the inventor has surprisingly discovered that TF is located in the endosomes of early-stage cancer and is located diffusely throughout the cytoplasm in late-stage cancer.

BRIEF DESCRIPTION OF THE DRAWINGS

FIGS. 2B -2E shows the details of the 58 matches identified in this assay.

FIG. 6 shows the amino acid sequences of the TF antigen epitopes (SEQ ID NOs: 9-25, respectively).

FIG. 7 shows the nucleotide sequence of Alper-TF mAb heavy chain (SEQ ID NO: 26).

FIG. 8 shows the nucleotide sequence of Alper-TF mAb light chain (SEQ ID NO: 27).

Figure 9B:
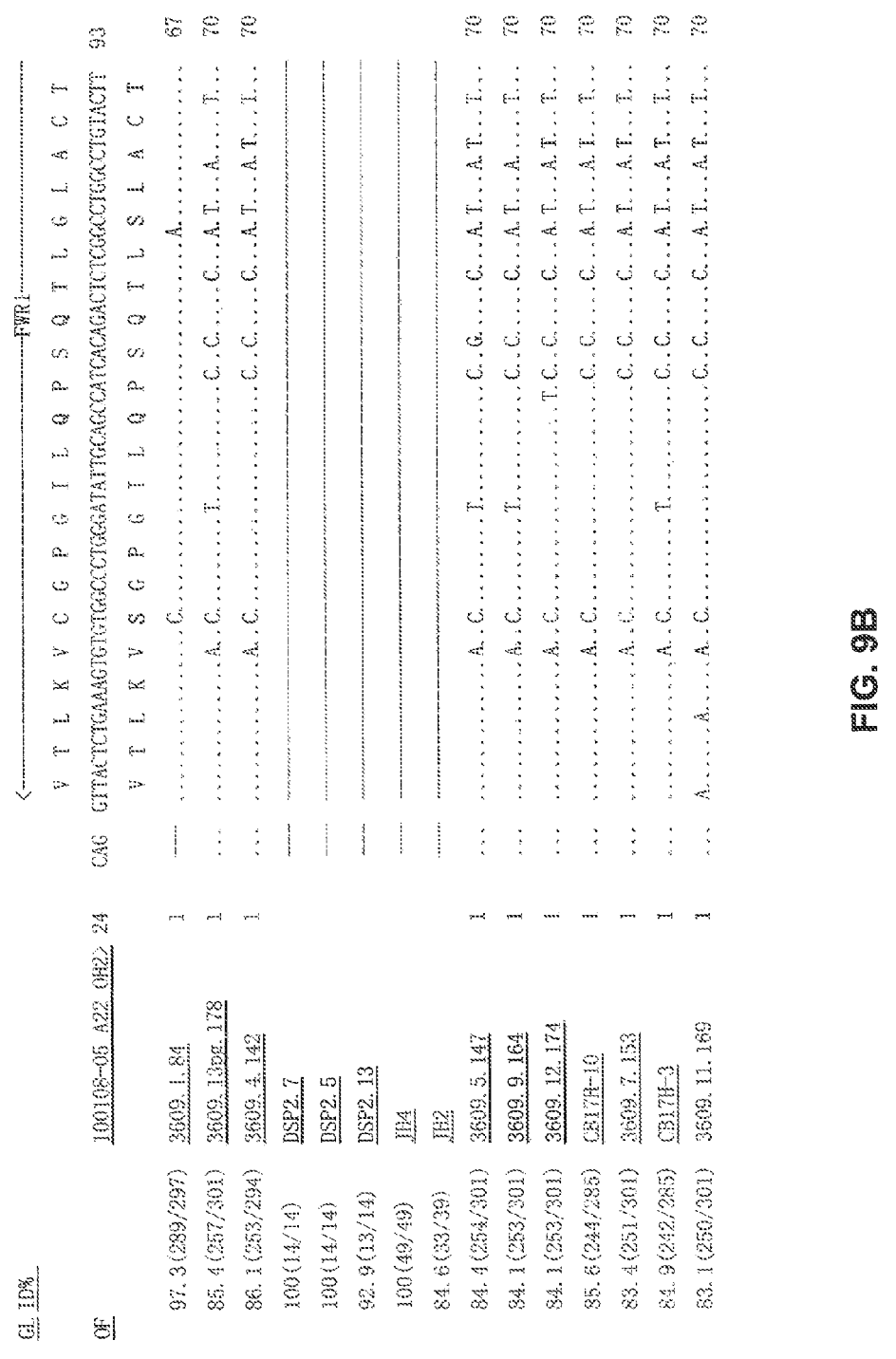
Figure 9C:
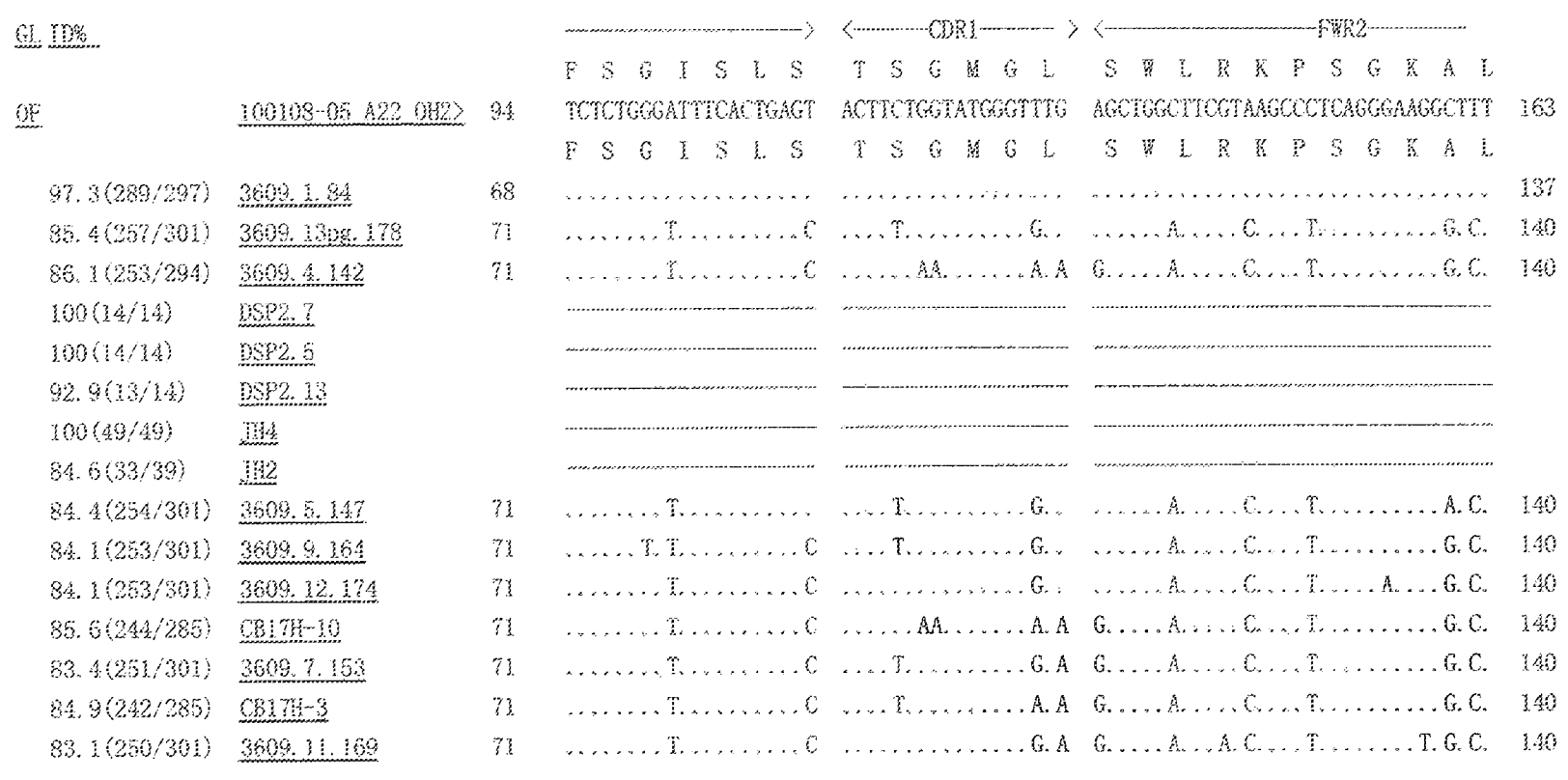
Figure 9D:
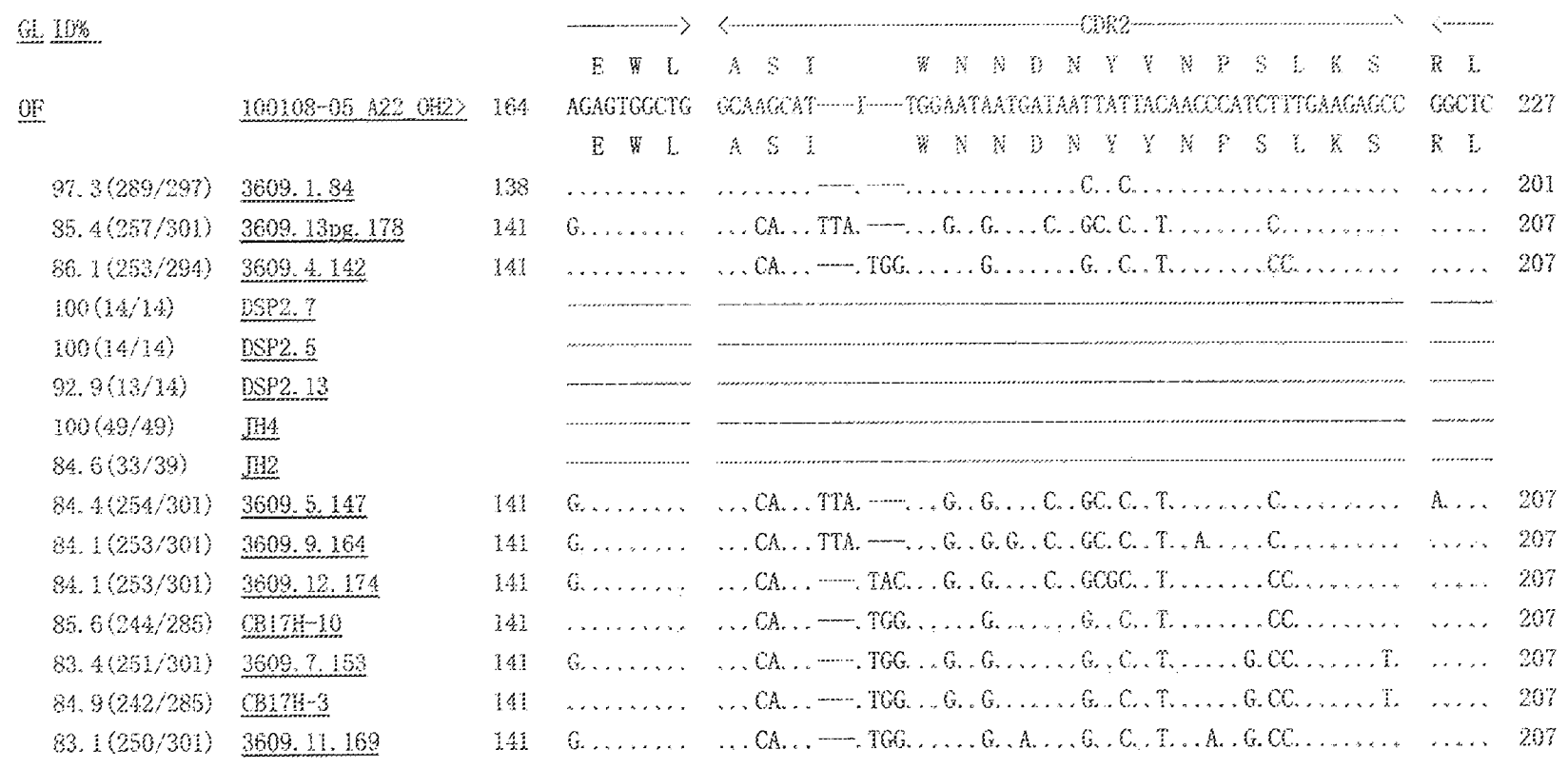
Figure 9E:
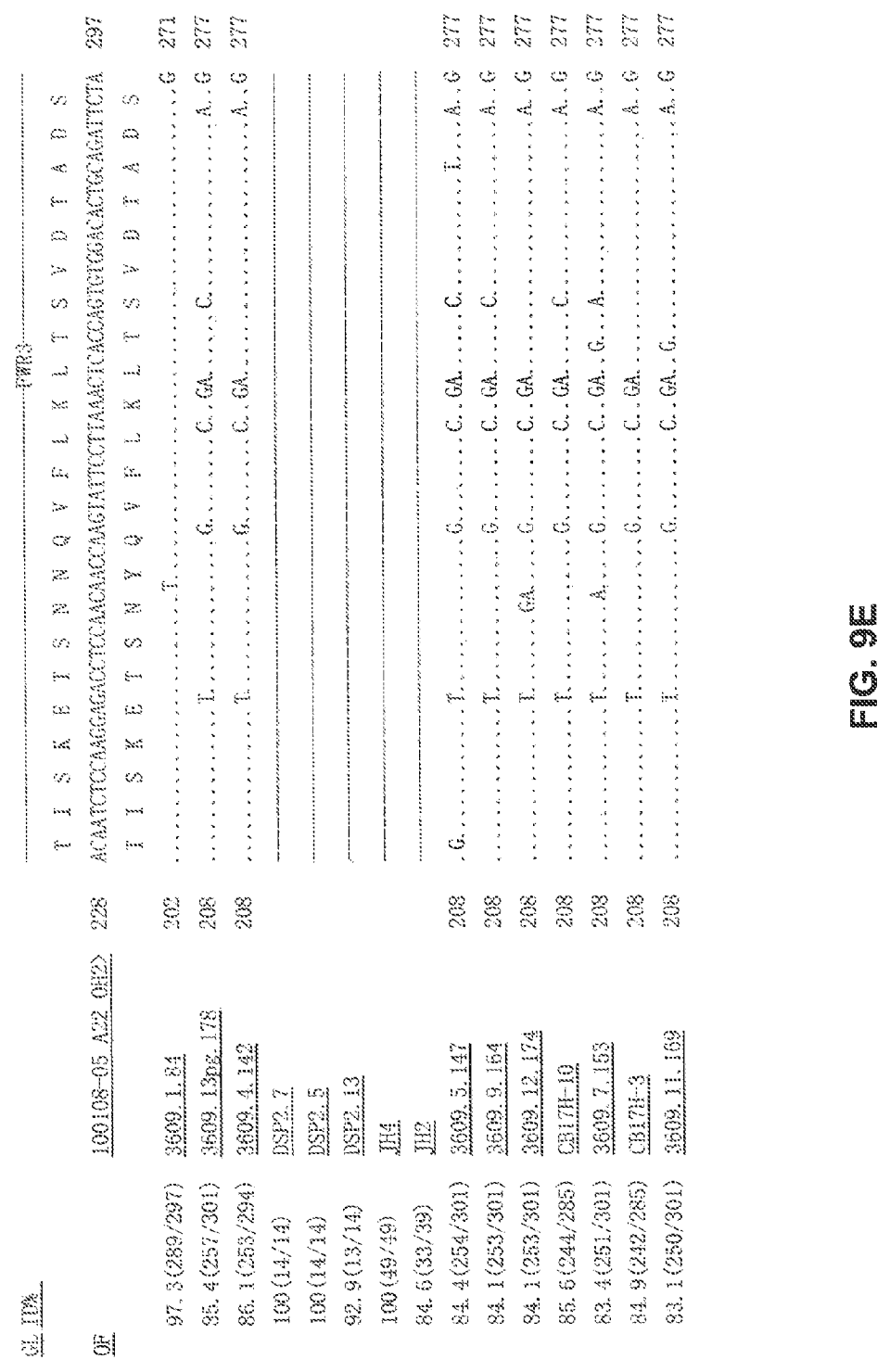
Figure 9F:
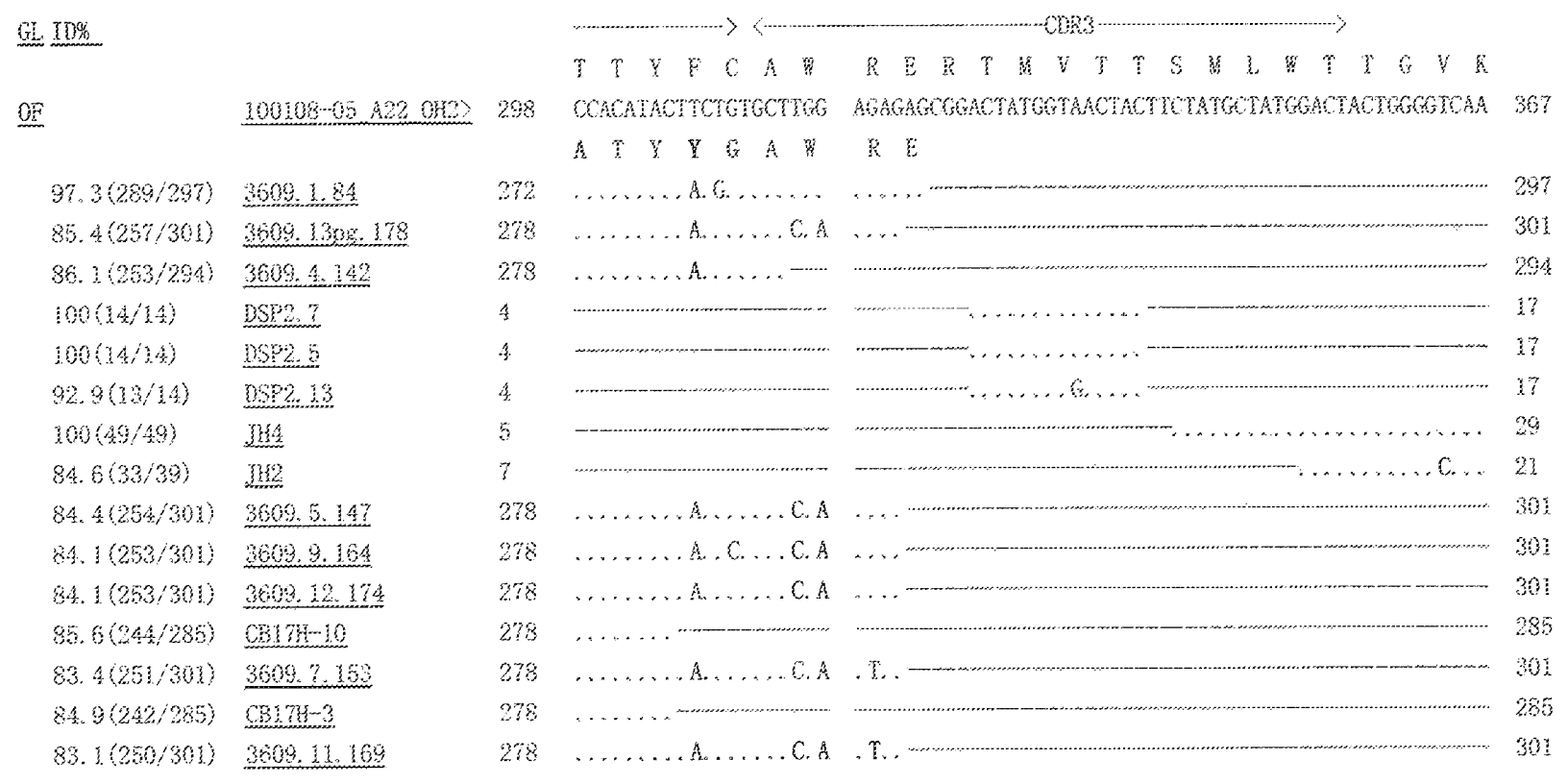

FIGS. 9A-G show, in the top line, the amino acid sequences of Alper-TF mAb heavy chain (SEQ ID NO: 1) and the heavy chain CDR1, CDR2, and CDR3 (SEQ NOs: 2, 3 and 4, respectively). The nucleotide sequence is provided in the second line (SEQ ID NO:26). Amino acid residues are numbered using the convention of Kabat et al., (1991) Sequences of Proteins of Immunological Interest, 5$^{th}$ Edition, Department of Health and Human Services, Public Health Service, National Institutes of Health, Bethesda (NIH Publication No. 91-3242). FIG. 9G also shows the sequences of the CDRs.

FIGS. 10A-10F show, in the top line, the amino acid sequences of Alper-TF mAb light chain (SEQ ID NO: 5) and the light chain CDR1, CDR2, and CDR3 (SEQ ID NOs: 6, 7 and 8, respectively). The nucleotide sequence is provided in the second line (SEQ ID NO:27). Amino acid residues are numbered using the convention of Kabat et al. FIG. 10F also shows the sequences of the CDRs.

FIG. 11A shows a representative image of the results of a direct immunofluorescence assay for Texas Red conjugated-TF (TxR-TF). As expected, TxR-TF, known endosomal marker, was incorporated into the endosomes during the 10-minute incubation, as demonstrated by the punctuate staining. FIG. 11B shows a representative image of the results of an indirect immunofluorescence assay for FITC-labled Alper-TF mAb. Alper-TF mAb fluorescence co-localized with all TxR-TF fluorescence in a similar punctuate manner.

BRIEF DESCRIPTION OF CERTAIN SEQUENCES

Figure 1:
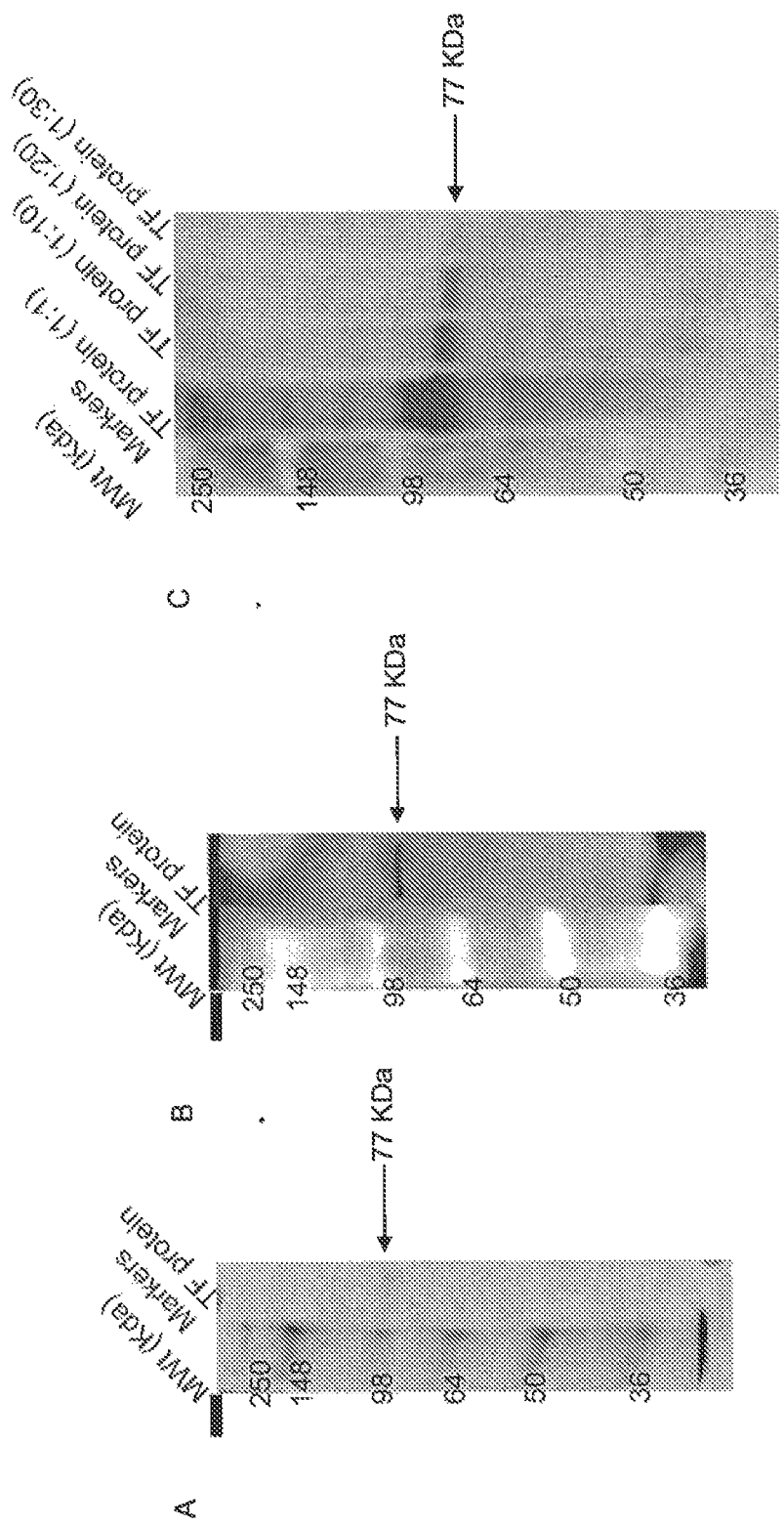
FIG. 1A is a Commassie Blue staining of the gel showing a single band at about 77 kDa.
FIG. 1B shows one representative image of the results of a Western Blot using Alper-TF mAb.
FIG. 1C shows another representative image of the results of a Western Blot using Alper-TF mAb.

SEQ ID NO: 1 shows the amino acid sequence of an Alper-TF mAb Heavy Chain

SEQ ID NO: 2 shows CDR1 of an Alper-TF mAb Heavy Chain

SEQ ID NO: 3 shows CDR2 of an Alper-TF mAb Heavy Chain

SEQ ID NO: 4 shows CDR3 of an Alper-TF mAb Heavy Chain

SEQ ID NO: 5 shows the amino acid sequence of Alper-TF mAb Light Chain

SEQ ID NO: 6 shows CDR1 of an Alper-TF mAb Light Chain

SEQ ID NO: 7 shows CDR2 of an Alper-TF mAb Light Chain

SEQ ID NO: 8 shows CDR3 of an Alper-TF mAb Light Chain

SEQ ID NOs: 9-25 show the amino acid sequence of potential TF epitopes.

SEQ ID NO 26: shows the nucleic acid sequence of an Alper-TF mAb Heavy Chain

SEQ ID NO 27: shows the nucleic acid sequence of an Alper-TF mAb Light Chain

DESCRIPTION OF EMBODIMENTS

The present invention provides an antibody capable of binding to a mature or precursor form of TF. In one aspect, the present invention includes a TF antibody and antigen binding fragments thereof that preferentially bind a TF antigen that is a 698 amino acid precursor protein. In certain embodiments, the antibody preferentially binds to a precursor form of TF, e.g., with a specific affinity of between $10^{-8}$ M and $10^{-11}$ M. In another aspect, the present invention provides an antibody capable of binding to a mature form of TF with or without post-translational modifications such as glycosylation or phosphorylation. In another embodiment, the antibody may preferentially bind to a mature form of TF, e.g., with a specific affinity of between $10^{-8}$ M and $10^{-11}$ M.

The present invention provides an antibody capable of selectively reducing the activity of a TF, e.g., in a sample or cell, including reducing the activity of a precursor TF.

In yet other aspects, the present invention provides an antibody capable of binding to a TF epitope consisting of any of SEQ ID NOs. 9-25, as shown in FIG. 6. In certain aspects, the present invention provides an antibody capable of preferentially binding to a precursor form of TF compared to a mature form of TF.

The present invention provides an antibody specific for TF, where the antibody comprises one or more of the heavy chain complementarity determining region (CDR) antigen binding site sequences set forth in SEQ ID NOs, 2-4, and one or more of the light chain CDR antigen binding site sequences set forth in SEQ ID NOs, 6-8. The antibody specific for TF may comprise all three heavy chain CDR antigen binding site sequences CDR1, CDR2, and CDR3 as set forth in SEQ ID NOs. 2-4, and all three light chain CDR antigen binding site sequences CDR1, CDR2, and CDR3 as set forth in SEQ ID NOs. 6-8. Contemplated is an anti-TF antibody that binds TF comprising a heavy chain variable domain comprising three complementarity determining regions (CDRs) comprising the amino acid sequences of SEQ ID NO: 2, SEQ ID NO:3, and SEQ ID NO:4, and a light chain variable domain comprising three CDRs comprising the amino acid sequences of SEQ ID NO: 6, SEQ ID NO:7, and SEQ ID NO:8. In one embodiment, the invention comprises an anti-TF antibody that binds to human TF, wherein the antibody binds to the same epitope as an antibody having a heavy chain comprising the sequence given in SEQ ID NO: 1 and a light chain comprising the sequence given in SEQ ID NO: 5.

In other aspects, the present invention provides an isolated DNA sequence which encodes the heavy chain of an antibody molecule, wherein the antibody molecule has specificity for TF and wherein the variable domain of said heavy chain comprises at least one CDR selected from the heavy chain CDRs of CDR1, CDR2, and CDR3 set forth in SEQ ID NOs. 2-4, and at least one CDR selected from the light chain CDRs of CDR1, CDR2, and CDR3 set forth in SEQ ID NOs. 6-8. In one embodiment the isolated DNA sequence comprises DNA encoding the amino acids of all three CDRs from the heavy chain, or all three CDRs from the light chain.

In yet other aspects, the present invention provides a method of characterizing TF expression of cells in a biological sample by (a) obtaining said sample; (b) contacting said sample with an antibody capable of preferentially detecting TF; and (c) determining quantity or localization of said TF.

In yet other aspects, the present invention provides an immunoassay for detecting TF in a biological sample. The immunoassay may comprise: (a) contacting a biological sample with an antibody described herein; and (b) qualitatively or quantitatively determining the formation of an immune complex of the antibody and TF. In one aspect the immunoassay is an ELISA. In another aspect the immunoassay is a sandwich ELISA.

In yet other aspects, the immunoassay is an immunocytochemical assay, including but not limited to an immunohistochemical or immunofluorescence assay. The immunocytochemical (ICC) assay may be performed on tissue, cells, whole blood, plasma, serum, or urine. The ICC assay may be used to detect TF. An ICC method is contemplated wherein a biological sample from a patient diagnosed with cancer or in need of diagnosis is contacted with an antibody described herein; and the formation of immune complex of the antibody and TF is qualitatively or quantitatively determined. The level and localization of TF can provide a diagnosis of cancer when compared to a healthy noncancerous control or when compared to an earlier sample from the same patient. As described herein, TF is increased in cancer. Importantly, localization of TF to the endosomes (punctuate cytoplasmic staining), as well as localization to the cytoplasm in the absence of punctuate staining, indicates a diagnosis of cancer. Early stage cancer can be detected and diagnosed by localization of TF to endosomes (punctuate cytoplasmic staining). Late stage cancer can be detected and diagnosed by localization to the cytoplasm in the absence of punctuate/ endosomal staining.

In each method and use described herein, the biological sample may be selected from tissue, cells, whole blood, serum, plasma, and urine. The biological sample may be selected from a human subject diagnosed with cancer or from a human subject in need of diagnosis of cancer. In one aspect, the cancer is prostate cancer.

In yet other aspects, the present invention provides a method of characterizing TF expression of cells in a sample comprising: (a) obtaining a sample from a subject; (b) contacting the sample with an antibody capable of preferentially detecting a precursor form of TF antigen; and (c) determining the quantity or localization of the antigen.

Definitions

Antibody: This refers to single chain, two-chain, and multi-chain proteins and glycoproteins belonging to the classes of polyclonal, monoclonal, chimeric and hetero immunoglobulins; it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Monoclonal Antibody: This refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a $V_H$ and a $V_L$ where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions. Humanized antibodies can or cannot be considered chimeric.

Humanized Antibody: This refers to an antibody derived from a non-human antibody. The humanized antibody retains or substantially retains the antigen-binding properties of the parent antibody but is less immunogenic in humans than its parent antibody.

Antibody Conjugates, Fusion Proteins, and Bispecific Antibodies; These refer to monoclonal antibodies conjugated by chemical or non-chemical methods with radionuclides, drugs, macromolecules, or other agents.

Alper-TF mAb: This term refers to an antibody comprising a heavy chain variable domain comprising at least one CDR selected from the group consisting of: the amino acid sequence of SEQ ID NO: 2, the amino acid sequence SEQ ID NO:3, and the amino acid sequence SEQ ID NO:4, and a light chain variable domain comprising at least one CDR selected from the group consisting of: the amino acid sequence of SEQ ID NO: 6, the amino acid sequence of SEQ ID NO:7, and the amino acid sequence of SEQ ID NO:8.

Antigen: This refers to one or more molecules or one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of antigen to antibody must be above background levels.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids, and are shown in FIG. 6, and in the sequence listing.

Complementarity Determining Region, or CDR: This refers to amino acid sequences which together define the binding affinity and specificity of the natural Fv region of a native immunoglobulin binding site. The light and heavy chains of an immunoglobulin each have three CDRs. The numbering convention delineated by Kabat et al., (1991) Sequences of Proteins of Immunological Interest, 5th Edition, Department of Health and Human Services, Public Health Service, National institutes of Health, Bethesda (NIH Publication No. 91-3242) is used where no other numbering is provided.

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues that are unique to Alper-TF mAb when compared to other IgGs. Preferentially, the SDR is the part of an immunoglobulin that is directly involved in antigen contact. The sequence of the CDRs may be altered at any residue except those indicated as an SDR.

Constant Region: This refers to the portion of an antibody molecule which confers effector functions. A heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. A light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to TF.

Immunoreactivity: A measure of the ability of an immunoglobulin to recognize and bind to a specific antigen.

TF Antibodies or TF mAbs: These terms refer to antibodies that bind to proteins that are specifically bound by the same protein as a protein with the epitope for Alper-TF mAb as shown in FIG. 6 (SEQ ID NO: 9-25), which may be a modified or precursor form of the protein that is produced by cancer cells. The antibodies include variants, such as chimeric, humanized, and other variants known to those skilled in the art, TF antibodies are said to be specific for a TF antigen if they exhibit preferential binding to the same TF antigen as bound by Alper-TF mAb at least 85% of the time, at least 90% of the time, or, in a preferred aspect, at least 95% of the time relative to any other protein.

TF Antigens: This term refers to expression products bound by Alper-TF mAb, which can be used as antigens, target molecules, biomarkers, or any combination thereof. A TF antigen can be produced by a TF gene and homologues of a TF gene and can include various modifications, precursor forms, mature forms, or secreted forms of TF bound by Alper-TF mAb and produced by a cell expressing that TF antigen, such as a cancer cell.

Substantially Similar Binding Properties: This refers to an antibody, such as a humanized antibody or fragments thereof which retain the ability to preferentially bind an antigen recognized by the parent antibody used to produce the antibody, such as a humanized antibody, or fragments thereof. Preferably, the affinity of a chimeric antibody, humanized antibody, or antibody fragment is at least about 10% of the affinity of the parent antibody, more preferably at least about 25%, even more preferably at least about 50%. Most preferably, a chimeric antibody, preferably a humanized antibody, or antibody fragments thereof exhibit an antigen-binding affinity that is at least about 75% of the affinity of the parent antibody. Methods for assaying antigen-binding affinity are known in the art and include half-maximal binding assays, competition assays, and Scatchard analysis. In a preferred aspect, antigen-binding affinity is assayed using a competition assay.

Substantially Homologous: This refers immunoglobulin sequences that exhibit at least about 85% identity, more preferably about 90% identity, most preferably about 95% identity with a reference itnmunoglobulin sequence, where % identity is determined by comparing the number identical of amino acid residues between the two immunoglobutins, where the positions of the amino acid residues are indicated using the Kabat numbering scheme.

Substantially pure; For the purpose of the present invention, substantially pure refers to a homogeneous preparation preferably of a TF antibody or antibody fragment, or other chemical or biological agents. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Immunocytochemistry: As used herein, immunocytochemistry (ICC) refers to assays that use antibodies to detect specific peptide, proteins, protein antigens, or epitopes that are bound by the antibodies. The antibodies may be labeled with a detection agent or non-labeled. Immunofluorescence is a type of immunocytochemistry that utilizes fluorescent detection, Immunohistochemistry (IHC) is a type of immunocytochemistry that specifically analyzes peptides, protein, protein antigens, or epitopes that are bound by the antibodies in sections of biological tissues.

Anti-TF Antibodies and Anti-TF Antibody Fragments

The present invention provides antibodies that bind to TF, including Alper-TF mAb, as well as anti-TF antibodies and antigen binding fragments thereof that are capable of binding to the same epitope as is bound by Alper-TF mAb. Antibodies or antibody fragments include those that are specific for at least one TF form, at least the same TF form bound by Alper-TF mAb. In certain embodiments, the antibodies and antibody fragments thereof can be used to detect a precursor and/or mature form of TF within tissues, cells, blood, serum, plasma, and urine.

The anti-TF antibodies and antibody fragments, including Alper-TF mAb, detect an approximately 77 kDa TF antigen. The antibodies and antibody fragments are useful in detecting cancer in tissues, cells, blood, serum, plasma, and urine. TF is increased in cancerous tissues, cells, blood, serum, plasma, and urine, when probed with an anti-TF antibody of the invention, and when compared to a non-cancerous control. In one aspect, the TF antigen preferentially bound by Alper-TF mAb is localized in the early endosomes of subjects with early-stage cancer, including prostate cancer. In another aspect, the TF antigen preferentially bound by Alper-TF mAb moves into late endosomes in cells of subjects with later stages of cancer. In one aspect, levels of soluble TF antigen in late endosomes of cancer cells are significantly associated with decreased survival relative to survival of patients with soluble TF antigen in early endosomes of prostate cancer cells, observed in patients with early-stage prostate cancer.

In yet another aspect, the TF antigen preferentially bound by Alper-TF mAb is localized to exosomes. Exosomes are nanometer-sized vesicles secreted by a wide range of mammalian cell types. Exosomes are a notable feature of cancer and malignancy. For example, exosome secretion is increased in cancer cells Tumor-antigen enrichment of exosomes is also associated with cancer cells. Mitchell et al, identified the utility of measuring PSA in exosomes concentrated from urine, finding that PSA was present in exosomes concentrated from the urine of 20 of 24 prostate cancer specimens but notably absent from healthy donor specimens. Journal of Translational Medicine. (2009) 7:4. One embodiment of the present invention includes TF antibodies and TF antibody fragments capable of detecting TF antigen in urinary exosomes. The detection of TF in urinary exosomes indicates the presence of cancer.

One embodiment includes TF antibodies and TF antibody fragments capable of binding to the same TF antigen as bound by Alper-TF mAb with a specific affinity of between $10^{-8}$ M and $10^{-11}$ M. Another embodiment includes a TF antibody or TF antibody fragment capable of selectively reducing the activity of such a TF antigen in a cell.

A TF antibody TF antibody fragment can be, without limitation, a monoclonal antibody, a chimeric antibody, a humanized antibody, or an antibody conjugate.

A TF antibody or TF antibody fragment can be any gamma globulin protein found in blood or other bodily fluids of vertebrates, and used by the host immune system to identify and neutralize foreign objects, such as bacteria and viruses. In another aspect, the antibody or antibody fragment can be selected from an antibody, a monoclonal antibody, a chimeric antibody, a humanized antibody, or an antibody conjugate. In yet another aspect, a TF antibody or TF antibody fragment can be any type of immunoglobulin protein, such as IgA, IgD, IgE, IgG or IgM.

In one aspect, a TF antibody or TF antibody fragment is capable of reducing the activity of that bound TF form, including a soluble precursor form. In another aspect, a TF antibody or TF antibody fragment is capable of reducing the activity of TF in a mature form.

In another aspect of the present invention, a TF antibody or TF antibody fragment is capable of preferentially binding to a mature form of TF protein. In one aspect of the present invention, a TF antibody or TF antibody fragment is capable of preferentially binding to a precursor form of TF protein. In another aspect of the present invention, TF antibody or TF antibody fragment is capable of binding to a mature or precursor form or forms of a TF antigen. In such aspects, such preferential binding of a TF antigen can be relative to any other protein. In a particular aspect, such preferential binding is relative to a mature TF antigen. In another particular aspect, such preferential binding to a TF antigen is relative to a TF that is nuclear bound or membrane associated. In another aspect of the present invention, antibodies or antibody fragments can be used to detect a mature form of TF.

In an aspect of the present invention, a TF antibody or TF antibody fragment is capable of preferentially binding to TF protein localized to endosomes. In another aspect of the present invention, a TF antibody or TF antibody fragment is capable of preferentially binding to TF protein localized to multivesicular bodies. In yet another aspect of the present invention, a TF antibody or TF antibody fragment is capable of preferentially binding to TF protein localized to exosomes. In such aspects, such preferential binding of a TF antigen can be relative to any other protein. In a particular aspect, such preferential binding is relative to TF protein localized to the cytoplasm. In another particular aspect, such preferential binding to a TF antigen is relative to TF protein that is nuclear bound or membrane associated.

In an aspect of the present invention, preferential binding is relative to background. In another aspect, the preferential binding is at least 2-fold, 3-fold, 4-fold, 5-fold, 10-fold, 100-fold, 1,000-fold, 10,000-fold or 1,000,000-fold increased relative to control. Methods for assaying antigen-binding affinity are known in the art and include half-maximal binding assays, competition assays, and Scatchard analysis, as set forth in Ausubel et al, Current Protocols in Molecular Biology (John Wiley & Sons Inc.). In a preferred aspect, antigen-binding affinity is assayed using a competition assay.

In an aspect, a TF antibody or TF antibody fragment binds TF or a particular form of TF such as a secreted, precursor form or a secreted, mature form, and/or a form with post-transcriptional processing such as phosphorylation or glycosylation, with a specific affinity of greater than $10^{-7}$M, $10^{-8}$M, $10^{-9}$M, $10^{-10}$M, or $10^{-11}$M, or between $10^{-8}$M-$10^{-11}$M, $10^{-9}$M-$10^{-10}$M and $10^{-10}$M-$10^{-11}$M. In a preferred aspect, specific activity is measured using a competitive binding assay as set forth in Ausubel.

TF antibodies and TF antibody fragments can optionally be immobilized on a solid phase, detectably labeled, or conjugated to a cytotoxic radionuclide, a cytotoxic drug, or a cytotoxic protein and the like. TF antibodies and TF antibody fragments can optionally be labeled. Labels include, but are not limited to, fluorescent and radioisotope labeling.

TF antibodies and TF antibody fragments of the present invention can detect TF in human cells, more preferably human cancer cells, such as cancer cells of human breast, ovary, cervix, prostate, colon, stomach, kidney, liver, head, neck, lung, blood, pancreas, skin, testicle, thyroid and brain. Expressed TF antigens can include any form of the gene product, although particularly preferred aspects relate to the detection of the soluble or secreted form of TF. Such antigens can also include gene-produced homologues of the TF gene and modified TF antigens expressed by cancer cells. In one aspect, the modified TF gene product is phosphorylated.

In one aspect, the TF antibodies and TF antibody fragments include those capable of binding to the TF epitopes comprising or consisting of those shown in FIG. 6, such as SEQ ID NOs: 9-25, or fragments of these amino acids. Antibodies or antibody fragments can preferentially be used to detect the TF epitopes comprising or consisting of those shown in FIG. 6, such as SEQ ID NOs: 9-25 or fragments of these amino acids. The invention also includes TF antibodies and TF antibody fragments specific to TF expression products that contain antigen binding sites that are substantially homologous to proteins comprising or consisting of the amino acids of SEQ ID NOs: 9-25 or that result in substantially similar binding properties. Such antibodies or fragments thereof can be capable of binding to epitopes that are 95%, 90%, 85%, or 80% identical to one or more of the TF epitopes comprising or consisting of those shown in FIG. 6, such as SEQ ID NOs: 9-25 or fragments of these amino acids.

Figure 10B:
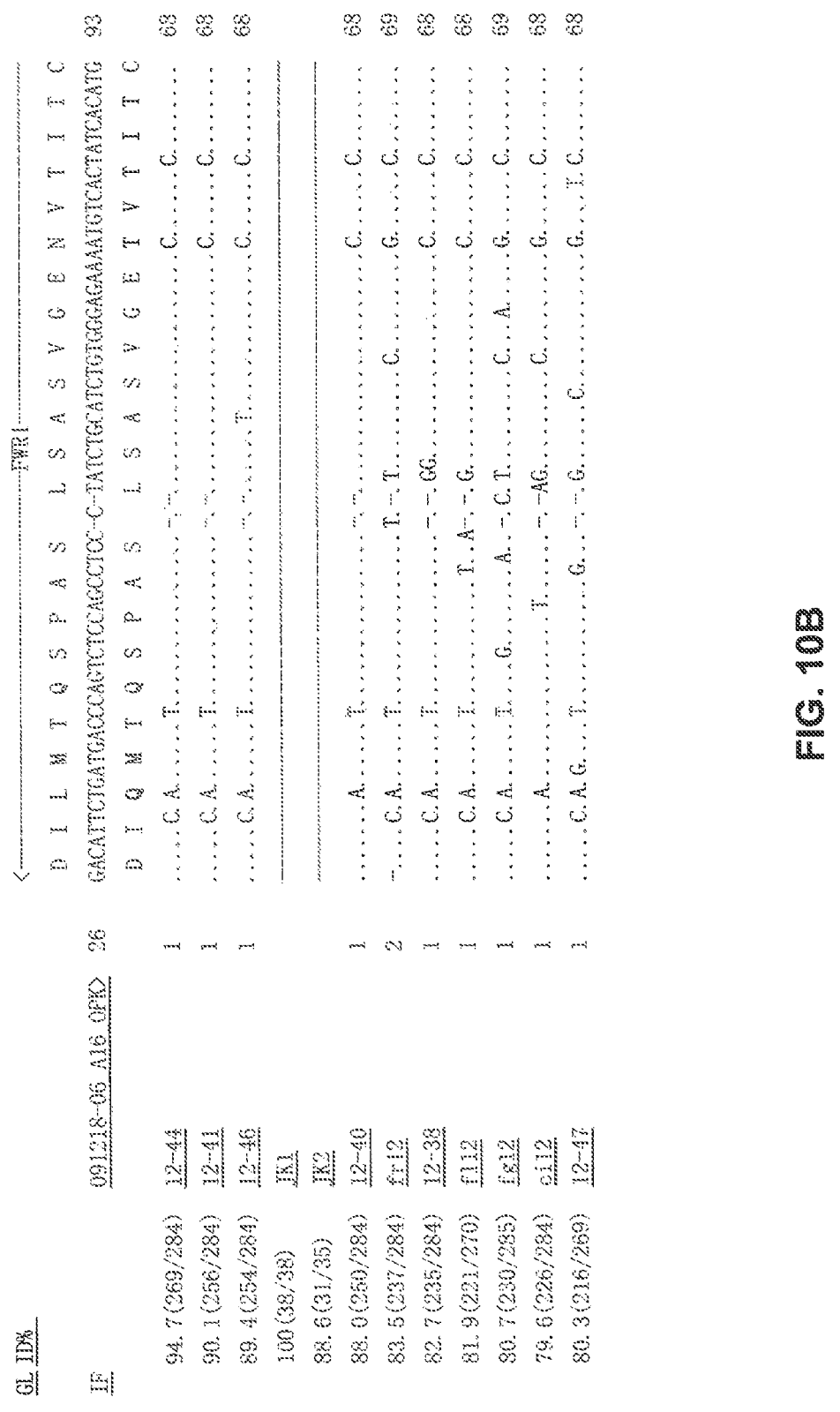
Figure 10D:
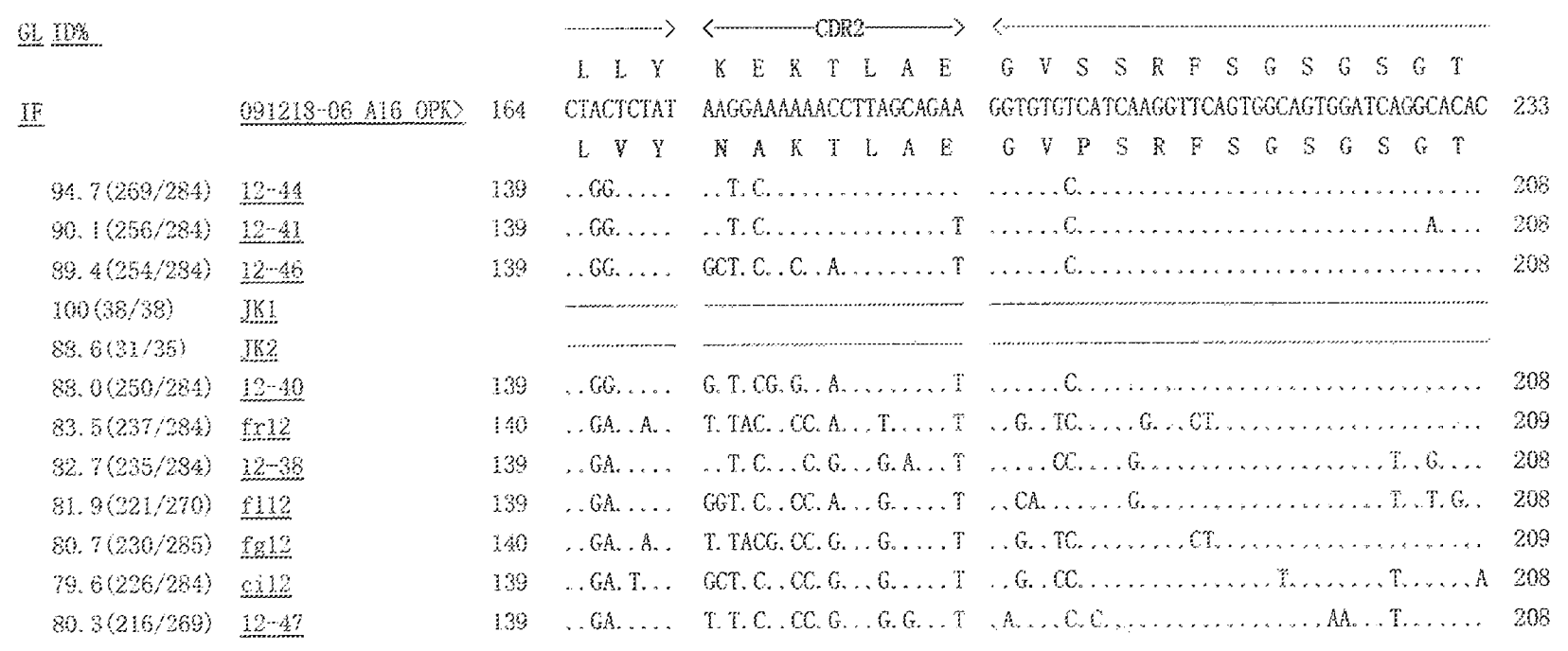
Figure 10E:
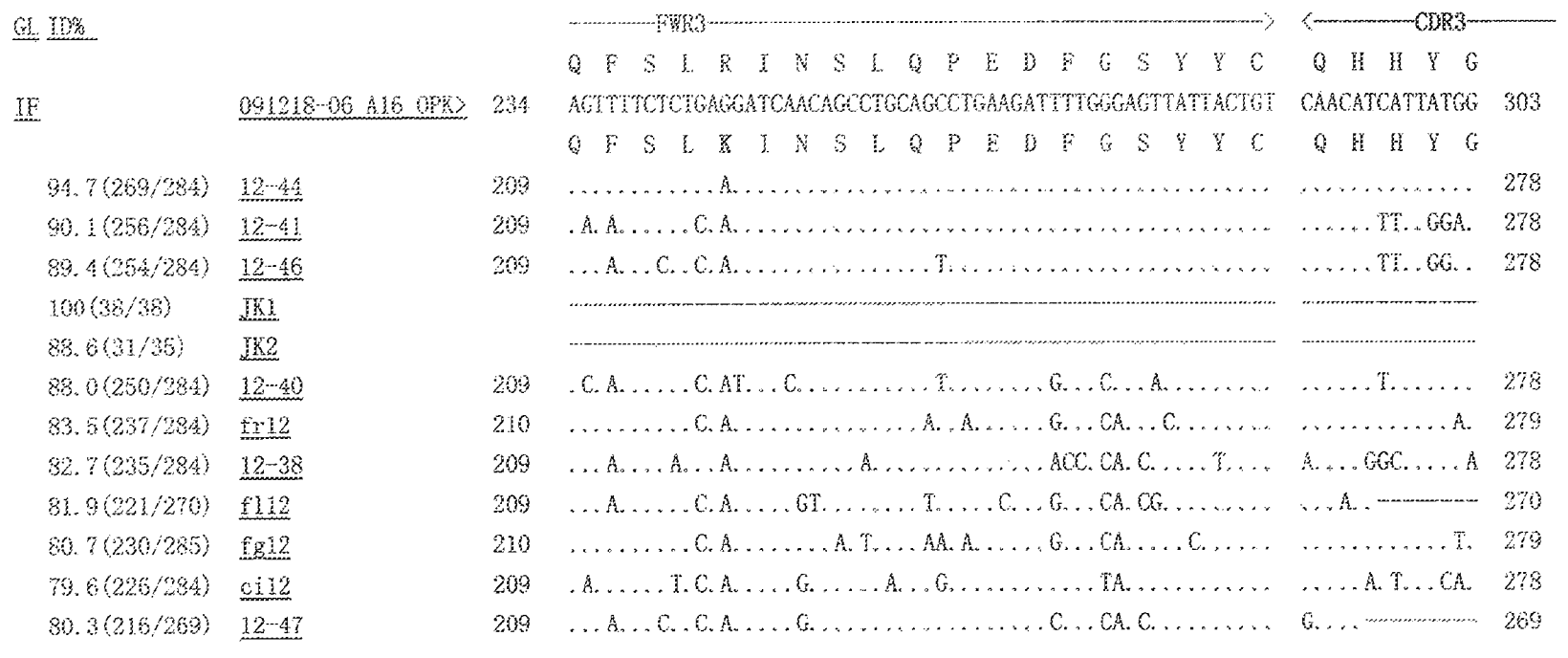

In another aspect, the present invention includes an antibody or an antibody fragment that binds TF, wherein the antibody comprises, consists of, or has, at least one of the heavy chain CDR antigen binding site amino acid sequences CDR1, CDR2, and CDR3 (SEQ ID NOs: 2, 3, and 4, respectively, as set forth in FIG. 9), and/or at least one of the light chain CDR antigen binding site amino acid sequences CDR1, CDR2 and CDR3 (SEQ ID NOs, 6, 7, and 8, respectively, as set forth in FIG. 10), A TF antibody or TF antibody fragment may include any single CDR shown in FIGS. 9 and 10, alone or in combination. By way of example, a TF antibody or TF antibody fragment may include CDR1 and CDR2 from both heavy and light chains of FIG. 9 (SEQ ID NOs.: 2, 3, 6, and 7, respectively). In other embodiments, a TF antibody or TF antibody fragment may include CDR1, CDR2, CDR3 from both heavy and light chains of FIG. 10 (SEQ ID NOs.: 2, 3, 4, 6, 7, and 8, respectively). In yet other embodiments, a TF antibody or TF antibody fragment may include the full heavy and light chain sequences illustrated in FIGS. 9 and 10 (SEQ ID NOs.: 1, 26 and 5, 27).

The invention also includes TF antibodies and TF antibody fragments specific to TF expression products that contain antigen binding sites that are substantially homologous to these or that result in substantially similar binding properties. Such antibodies or fragments thereof comprise sequences 95%, 90%, 85%, or 80% identical to one or more of the CDR1, CDR2, or CDR3 heavy or light chain from FIGS. 9 and 10. The present invention also includes hybridoma lines and the monoclonal antibody molecules that they secrete, which are specific to TF antigen expressed by normal or cancer cells. The present invention also includes chimeric antibodies, such as humanized, and antibody fragments and also includes other modified TF antibodies and TF antibody fragments.

In addition to the specific amino acid sequences of the antigen binding sites of the heavy and light chains set forth in FIGS. 9 and 10, the present invention also encompasses TF antibodies and TF antibody fragments that have preferential binding to TF antigens but which have FWR and/or CDR antigen binding site amino acid sequences that are not identical to those set forth in FIGS. 9 and 10. Such TF antibodies and TF antibody fragments are preferred if they are specific or preferentially selective for the TF antigen, preferably at least 85% or more as specific, more preferably at least 90% or more as specific, and most preferably at least 95% or more as specific for the TF antigen as the Alper-TF mAb or antibody fragment therefor. According to a preferred aspect, a variant of a TF antibody or TF antibody fragment of the present invention can be as specific for the TF antigen as a non-variant antibody or antibody fragment of the present invention, or can be more specific.

TF antibodies and TF antibody fragments that are specific to TF but which have FWR and/or CDR antigen binding site amino acid sequences that are not identical to those set forth in FIGS. 9 and 10 can possess the same or different specificity determining regions (SDRs) as the FWRs and/or CDRs of FIGS. 9 and 10 (set forth in Tables 1 and 2).

Modifications to the amino acid sequences of the antigen binding sites CDR1, CDR2, and CDR3 set forth in FIG. 9 (heavy chain) and FIG. 10 (light chain) can occur in either or both of the FWR and CDR sequences. According to certain aspects of the invention, variations in antibodies or antibody fragments can occur where they have substantially homologous amino acid sequences, substantially similar binding properties, or both.

Humanized variants of the antibodies or antibody fragments of the invention can contain a reduced murine content, and potentially, reduced immunogenicity, when compared to murine antibodies, such as Alper-TF mAb, or antibody fragments thereof. Humanized variants include those that retain a binding affinity that is substantially similar to that of the original antibody or antibody fragment. An aspect of the invention provides CDR variants of humanized TF antibodies or antibody fragments in which 1, 2, 3, 4, 5, or 6 (three heavy chain and three light chain) CDRs are humanized. A second aspect of the invention provides SDR variants of humanized TF antibodies and TF antibody fragments in which only Specificity Determining Residues (SDRs) from the TF antibodies and TF antibody fragments are present in the humanized antibodies. The SDRs are selected from Table 1 or Table 2.

TABLE 1

Specificity-Determining Residues in Alper-TF mAb Heavy Chain (SEQ ID NO. 1).

| Position | Residue |
|---|---|
| 6 | C |
| 18 | G |
| 76 | N |
| 91 | T |
| 94 | F |
| 95 | C |

TABLE 2

Specificity-Determining Residues in Alper-TF mAb Light Chain (SEQ ID NO. 5).

| Position | Residue |
|---|---|
| 3 | L |
| 18 | N |
| 48 | L |
| 50 | K |
| 51 | E |
| 59 | S |
| 74 | R |
| 94 | I |

CDR variants can be formed by replacing at least one CDR of a humanized TF antibody and antibody fragments with a corresponding CDR from a human antibody. CDR variants include those in which one, two, three, four, five, or six CDRs are replaced by a corresponding CDR from a human antibody and retain biological activity that is substantially similar to the binding affinity of the parental TF mAb. CDR variants of the invention can have a binding affinity that is 25% more than the binding affinity of the parental TF antibody or antibody fragment, more preferably more than 50%, and most preferably more than at least 75% or 90%.

CDR variants can have altered immunogenicity when compared to TF antibodies and TF antibody fragments can be formed by grafting all six (three heavy chain and three light chain) CDRs from the TF antibodies and TF antibody fragments of the present invention onto the variable light ($V_L$) and variable heavy ($V_H$) frameworks of human TF antibodies and TF antibody fragments. However, less than all six of the CDRs of the TF antibodies and TF antibody fragments of the present invention can be present, while still permitting an antibody of the present invention to retain activity. Residues that are directly involved in antigen contact, such as Specificity Determining Residues (SDRs), can be refined. SDR variants are formed by replacing at least one SDR of the TF antibody or antibody fragment with a residue at a corresponding position from a human antibody. It should be noted that not all CDRs must include SDRs.

In a preferred aspect, the variants of the present TF antibodies and TF antibody fragments include a combination of CDR and/or SDR substitutions to generate variants having reduced immunogenicity in humans and a binding affinity that is substantially similar to that of the parental antibody or antibody fragment to TF.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis and random mutagenesis.

Alternatively, polypeptide fragments comprising only a portion of the primary antibody structure can be produced where the fragment substantially retains the immunoreactivity properties of the variant. Such polypeptide fragments include fragments produced by techniques known in the art, such as proteolytic cleavage of intact antibodies or fragments produced by inserting stop codons at the desired locations in the nucleotide sequence using site-directed mutagenesis. Single chain antibodies and fusion proteins which include at least an immunoreactivity fragment of the variant are also included within the scope of the invention.

TF antibodies and TF antibody fragments can optionally be immobilized on a solid phase, detectably labeled, or conjugated to a cytotoxic radionuclide, a cytotoxic drug, or a cytotoxic protein and the like.

The antibodies and their variants in accordance with the present invention can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of TF, including cancer, such as cancer of the breast, ovary, cervix, prostate, colon, stomach, kidney, liver, head, neck, lung, blood, pancreas, skin, testicle, thyroid and brain, most preferentially human breast, ovary, head, neck, brain, and prostate, in particular human prostate cancer. The pharmaceutical compositions are preferably administered to a mammal, more preferably a human patient in need of such treatment, in order to treat the disease.

TF antibodies and TF antibody fragments can either be labeled or unlabeled. Unlabeled antibodies can be used in combination with other labeled antibodies (secondary antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available and known in the art.

In one embodiment, an isolated antibody that binds serotransferrin (TF) is contempleated. The isolated antibody comprises a heavy chain variable domain comprising three complementarity determining regions (CDRs) comprising the amino acid sequences of SEQ ID NO: 2, SEQ ID NO:3, and SEQ ID NO:4 and a light chain variable domain comprising three CDRs comprising the amino acid sequences of SEQ ID NO: 6, SEQ ID NO:7, and SEQ ID NO:8.

In another aspect, an isolated antibody that binds TF is contemplated, wherein the antibody binds to the same epitope as an antibody comprising a heavy chain variable domain comprising the amino acids of SEQ ID NO: 1 and alight chain variable domain comprising the amino acids of SEQ ID NO: 5.

Also encompassed is an isolated antibody that comprises a heavy chain variable domain comprising the amino acids of SEQ ID NO:1 and a light chain variable domain comprising the amino acids of SEQ ID NO:5.

The isolated antibody of the invention recognizes a soluble protein having a molecular weight of about 77 kilodaltons as measured by gradient polyacrylamide gel electrophoresis.

The isolated antibody is capable of binding to a precursor form of TF with a specific affinity of between $10^{-8}$ M and $10^{-11}$ M.

The isolated antibody is also capable of binding to a mature form of TF with a specific affinity of between $10^{-8}$ M and $10^{-11}$ M.

Encompassed is an isolated antibody that recognizes at least one epitope selected from the group consisting of the amino acids of: SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25, or fragments of these amino acids.

An isolated antibody described herein that is immobilized on a solid phase is contemplated.

The isolated antibody described herein may be conjugated to an agent selected from the group consisting of: a detectable label, a cytotoxic radionuclide, a cytotoxic drug, and a cytotoxic protein.

An isolated DNA molecule which encodes the antibody described herein, as well as isolated vectors comprising DNA that encodes the heavy and/or light chain described herein is encompassed.

A kit comprising: an isolated antibody comprising a heavy chain variable domain comprising three complementarity determining regions (CDRs) comprising the amino acid sequences of SEQ ID NO: 2, SEQ ID NO:3, and SEQ ID NO:4 and a light chain variable domain comprising three CDRs comprising the amino acid sequences of SEQ ID NO: 6, SEQ ID NO:7, and SEQ ID NO:8 and a secondary antibody that binds to the antibody, wherein the secondary antibody is conjugated to a detectable label is encompassed.

A composition comprising a tissue specimen and an antibody-antigen complex between the antibody described herein and TF within the tissue specimen is encompassed.

A pharmaceutical composition comprising the antibody described herein in combination with a pharmaceutically acceptable carrier is contemplated.

Nucleic Acid Molecules and Host Cells

Any of the antibodies or antibody fragments of the present invention can be encoded by nucleic acids. The present invention includes such molecules, fragments of such molecules, and such molecules included in vectors and the like. Nucleic acid molecules also include the complement of such nucleic acid molecules. Both DNA and RNA molecules are examples of nucleic acid molecules.

In another aspect, the present invention provides an isolated DNA sequence which encodes the heavy chain of an antibody molecule, where the antibody molecule has preferential binding for TF antigens, including at least TF, and where the variable domain of the heavy chain comprises a CDR having the antigen binding site amino acid sequences of at least one, two, or all three CDR1, CDR2, and CDR3 set forth in FIG. 9.

In yet another aspect, the present invention provides an isolated DNA sequence which encodes the light chain of an antibody molecule, where the antibody molecule has preferential binding for TF antigens, including at least TF, and further where the variable domain of the light chain comprises a CDR having the antigen binding site amino acid sequences of at least one, two or all three CDR1, CDR2, and CDR3 set forth in FIG. 10.

in another aspect, the present invention includes a nucleic acid molecule in a host cell. Such nucleic acid molecule can be integrated into the genome of the host cell or can be present on a vector such as a plasmid or viral vector. A nucleic acid molecule of the present invention may be transiently present in such a host cell. In one aspect, a host cell is selected from the group B, *E. coli; Bacilli*, including *Bacillus subtilis; enterobacteriacae*, including *Salmonella, Serratia* and *Pseudomonas*, yeast, including *Saccharomyces; Pichia pastoris*; Sf9 insect cells; Sp2/0, VERO and HeLa cells, Chinese hamster ovary (CHO) cell lines; W138, BHK, COS-7, and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145, and LNCap cells.

Methods of Making TF Antibodies or Antibody Fragments

TF antibodies or antibody fragments of the present invention can be developed, for example, using the human prostate cancer cell line OPCT1, derived from prostate tumor epithelium resected from a patient who received no chemotherapy, radiotherapy, or hormone treatment (TlcN0M0; Gleason 3+3; available from Asterand Inc.).

The present invention includes processes for producing monoclonal chimeric antibodies, including humanized, using recombinant DNA technology. See, for example, Antibodies, A Laboratory Manual (Harlow & Lane Eds., Cold Spring Harbor Press, 1988), which is herein incorporated by reference in its entirety.

TF antibodies or antibody fragments of the present invention can be produced by any known method including, without limitation, generating murine hybridomas which produce antibodies or antibody fragments specific for TF. Hybridomas can be formed, for example, by the fusion of a mouse fusion partner cell and spleen cells from mice immunized against native TF prepared without fixation. Mice can be also immunized with crude or semi-purified preparations containing an antigen of interest, such as a native TF isolated without fixation. To immunize the mice, a variety of different conventional protocols can be followed. For example, mice can receive primary and boosting immunizations of antigenic preparations.

Cell fusions can be accomplished by any procedures known to those skilled in the field of immunology. Fusion partner cell lines and methods for fusing and selecting hybridomas and screening for antibodies or antibody fragments are known.

Antibodies or antibody fragments of the present invention can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the TF antibodies and TF antibody fragments can be produced by culturing hybridoma cells in vitro and isolating the secreted antibody or antibody fragment from the cell culture medium.

TF antibodies or antibody fragments of the present invention can also be produced by expressing the appropriate DNA sequence in a host after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of an TF antibody or antibody fragments can be inserted into separate expression vectors, or into the same expression vector.

Suitable hosts include, without limitation, prokaryotic strains such as *E. coli; Bacilli*, including *Bacillus subtilis; enterobacteriacae*, including *Salmonella, Serratia* and *Pseudomonaso*. Suitable hosts also include eukaryotic hosts such as yeast, including *Saccharomyces; Pichia pastoris;* SP9 insect cells; Sp2/0, VERO and HeLa cells, Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells, can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Isolated or purified DNA sequences can be incorporated into a cloning or expression vector, which can in turn be used to transform a host cell. The transformed host cells can be used in a process for the production of an antibody molecule having specificity for TF antigens, including culturing the host cells and isolating the antibody molecules they produce.

Diagnostic Methods, Assays, and Kits

In one embodiment, an in vitro method for detecting serotransferrin (TF) in a biological sample, comprising: (a) contacting a biological sample with the antibody of claim 1 or claim 2; and (b) qualitatively or quantitatively determining the formation of an immune complex between the antibody and TF, is encompassed. The biological sample may be from a human subject in need of diagnosis of prostate cancer. The biological sample may be from a human subject diagnosed with prostate cancer. The formation of an immune complex between the antibody and TF indicates the presence of cancer. The biological sample may be selected from tissue, cells, blood, serum, plasma, urine, and exosomes purified from urine.

In another embodiment, an in vitro method for diagnosing early and late-stage prostate cancer in a human subject comprising: (a) isolating a tissue or cell sample from a subject; (b) contacting the tissue or cell sample with the antibody of claim 1 or claim 2; (c) labeling the sample with an agent that detects the antibody; (d) visualizing the location of the labeled antibody within the tissue or cell; and (e) diagnosing early stage prostate cancer if the labeled antibody is located within an endosome, and diagnosing late stage prostate cancer if the labeled antibody not within an endosome is contemplated.

In another aspect, a method for diagnosing cancer in humans comprising: (a) removing a specimen from a patient suspected of having a cancer; (b) contacting the specimen with an effective binding amount of the antibody of claim 1 or claim 2, thereby forming antigen-antibody complexes in said specimen; (c) labeling the specimen with a label specific for the antigen-antibody complex; (d) detecting the presence of the antigen-antibody complex by detecting the label; and (e) diagnosing cancer if at least one antigen-antibody complex is detected is encompassed.

The cancer may be selected from the group consisting of human breast, prostate, ovary, head, neck, and brain.

In a further aspect, the present invention includes an immunoassay for preferentially detecting a TF antigen preferentially bound by a Alper-TF mAb, where the assay comprises using a TF antibody or TF antibody fragment of the present invention.

The present invention also includes an assay for preferentially detecting one or more TF antigens, including a TF antigen, which binds to a monoclonal antibody having one or more of the heavy chain CDR antigen binding site amino acid sequences set forth in FIG. 9, such as SEQ ID NOs: 2-5, and one or more of the light chain CDR antigen binding site amino acid sequences set forth in FIG. 10, such as SEQ ID NOs: 6-8. The detection can be in vitro or in vivo.

Such assays can be used in any suitable manner, including, without limitation, by comprising: (a) contacting the sample with an effective binding amount of one of the TF antibodies or TF antibody fragments of the invention; and (b) detecting the TF antigen by detecting the preferential binding of the antibody to a TF antigen. Assays of the present invention can be used to detect cancer in tissues, cells, blood, serum, plasma, or urine. The immunoassay can detect TF, including, TF that has been post-transcriptionally processed, and a soluble secreted precursor TF. The TF secreted from cancer cells is unique, and is surprisingly detected by the Alper-TF mAb of the present invention. This unique secreted TF antigen is upregulated in cancer, tumors, carcinoma cells, and in neoplastic disease cells selected from the group consisting of breast, ovarian, cervical, prostate, colon, stomach, kidney, liver, head, neck, lung, blood, pancreatic, skin, testicular, thyroid and brain cancers, and human prostate.

In a further aspect, the present invention provides a kit for the immunocytochemical detection, including but not limited to immunohistochemical or immunofluorescent detection, of carcinoma comprising: (a) a TF antibody or TF antibody fragment of the present invention, such as Alper-TF mAb; and (b) a secondary antibody conjugated to a detectable label. In an aspect, the detection can be in vitro and is for prostate cancer detection.

The present invention also includes a kit with a TF antibody or TF antibody fragment of the present invention, such as Alper-TF mAb, that detects a TF antigen preferentially bound by Alper-TF mAb in the early endosome, most preferably in prostate cancer cells of early stage prostate cancer subjects. The TF antigen preferentially bound by Alper-TF mAb is localized to the late endosomes in prostate cells, most preferably in subjects with later stages of prostate cancer. In one aspect, levels of soluble TF antigen in late endosomes of prostate cancer cells are significantly associated with decreased survival relative to survival of patients with soluble TF antigen in early endosomes of prostate cancer cells, observed in patients with early-stage prostate cancer. In yet another aspect, the TF antibody or TF antibody fragment included in the kit preferentially binds TF antigen in exosomes, preferably exosomes located in the extracellular space, blood, plasma, serum, or urine.

In a further aspect, the present invention provides a kit comprising a TF antibody or TF antibody fragment; and a secondary antibody conjugated to a detectable label. In an aspect, the detection can be in vitro and is for prostate cancer detection.

In a further aspect, the present invention provides a kit for the immunocytochemical detection, including but not limited to immunohistochemical or immunofluorescent detection, of carcinoma comprising: (a) a monoclonal antibody having one or more of the heavy chain CDR antigen binding site amino acid sequences set forth in FIG. 9, such as SEQ ID NOs: 2-5, and one or more of the light chain CDR antigen binding site amino acid sequences set forth in FIG. 10, such as SEQ ID NOs: 6-8; and (b) a secondary antibody conjugated to a detectable label.

All of the kits described herein may include reagents for assaying a sample for a TF antigen, such as, for example, buffers, instructions, TF antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of one or more TF antigens in a sample; and the like. Other examples of kits or kit formats are found in Alper, US Publication No. 20080293162, herein incorporated by reference in its entirety.

In further aspect, the present invention provides a method for diagnosing cancer, such as prostate cancer, in humans comprising: (a) removing a specimen from a patient suspected of having a cancer; (b) contacting the specimen with a TF antibody or TF antibody fragment of the present invention; (c) labeling the specimen; and (d) detecting the presence of the antigen-antibody complex by the label. Detection of at least one antigen-antibody complex indicates a diagnosis of cancer, in an aspect, the specimen can be one or more of a tissue sample, cell sample, blood, serum, plasma, and urine. In an aspect, a cancer subject may have a greater amount of TF antigen in serum than in plasma of the same subject. The difference in amount may be at least one order of magnitude to three orders of magnitude. The cancer may be selected from the group consisting of breast, ovarian, cervical, prostate, colon, stomach, kidney, liver, head, neck, lung, blood, pancreatic, skin, testicular, thyroid and brain cancers, and human prostate. In another aspect, a prostate cancer subject may have a greater amount of TF antigen in his urine than in the urine of a healthy subject.

In a still further aspect, the present invention provides a method for diagnosing prostate cancer in humans comprising: (a) removing a specimen from a patient suspected of having a prostate cancer; (b) contacting the specimen with a monoclonal antibody having one or more of the heavy chain CDR antigen binding site amino acid sequences set forth in FIG. 9, such as SEQ ID NOs: 2-5, and one or more of the light chain CDR antigen binding site amino acid sequences set forth in FIG. 10, such as SEQ ID NOs: 6-8; (c) labeling the specimen; and (d) detecting the presence of an increase in antigen-antibody complex by the label in the prostate cancer specimen compared to a specimen from a normal subject without prostate cancer. In an aspect, the specimen can be at least one of a tissue sample, blood, serum, plasma, and urine.

The cancers being diagnosed include, without limitation, those that are selected from the group consisting of breast, ovary, cervix, prostate, colon, stomach, kidney, liver, head, neck, lung, pancreas, skin, testicle, thyroid and brain, in particular human prostate cancer.

In an aspect, TF levels are higher in prostate patients relative to age-matched healthy controls. The increase in prostate cancer patients compared to age-matched healthy controls may be at least about 200%, about 300%, about 400%, about 500% or about 600% in their plasma levels of a TF form preferentially bound by Alper-TF mAb. In another aspect, TF levels are higher in late-stage prostate cancer patients relative to age-matched healthy controls or an early-stage prostate cancer subject. In a third aspect, TF levels are higher in late-stage prostate cancer patients relative to age-matched healthy controls. In one aspect, the level of TF are higher in early-stage prostate cancer patients relative to age-matched healthy controls, and similar to healthy control levels during the late stage of prostate cancer. An increase in TF levels means that they are statistically significant relative to age-matched healthy controls. Levels similar to healthy control levels can mean that the levels are not statistically significant. In an aspect, the statistically significant differences in levels of TF have a p-value of $p<0.05$ as measured by an appropriate statistical test, such as the student's T-test or the Mann-Whitney test. In another aspect, the statistically significant differences in levels of TF have a p-value of $p<0.01$ as measured by an appropriate statistical test, such as the student's T-test or the Mann-Whitney test. In a further aspect, the statistically significant differences in levels of TF have a p-value $p<0.005$ as measured by an appropriate statistical test, such as the student's T-test or the Mann-Whitney test. In a further aspect, the statistically significant differences in levels of TF have a p-value of $p<0.001$ as measured by an appropriate statistical test, such as the student's T-test or the Mann-Whitney test.

In a further aspect, the present invention provides a method for diagnosing prostate cancer in a subject in need thereof comprising: (a) contacting a specimen from said subject with a TF antibody or TF antibody fragment of the present invention; (b) labeling the specimen; and (c) detecting an increase of TF in a patient with prostate cancer, where such prostate cancer can be in early-stage, mid-stage, or late-stage, most preferably, early- or mid-stage prostate cancer. In an aspect, the specimen can be at least one of a tissue, blood, serum, plasma, and urine. The detection can be in vitro or in vivo.

In a still further aspect, the present invention provides a method for diagnosing prostate cancer in humans comprising: (a) removing a specimen from a patient suspected of having a cancer; (b) contacting the specimen with a monoclonal antibody having one or more of the heavy chain CDR antigen binding site amino acid sequences set forth in FIG. 9, such as SEQ ID NOs: 2-5, and one or more of the light chain CDR antigen binding site amino acid sequences set forth in FIG. 10, such as SEQ ID NOs: 6-8; (c) labeling the specimen; and (d) detecting the presence of the antigen-antibody complex by the label, The cancer being assayed, diagnosed, evaluated, monitored and/or predicted can be any of early-, mid- or late-stage prostate cancer or a combination thereof.

Without limitation, the biological sample for all methods and uses described herein include tissue, cell, blood, serum, plasma, urine and exosomes in the urine.

In an additional aspect, the present invention includes a method for developing drugs useful in treating, diagnosing, or both treating and diagnosing diseases characterized by the expression of gene products of TF and homologues thereof, including identifying gene products expressed by TF and homologues thereof, and utilizing the gene products as biomarkers in the development and identification of drugs selected from the group comprising TF antibodies and TF antibody fragments, inhibiting peptides, siRNA, antisense oligonucleotides, vaccines, and chemical compounds, which specifically target the gene products.

A TF antibody or TF antibody fragment of the present invention can also be used in diagnosis of diseases characterized by the expression of TF, such as cancer. For example, in vivo diagnosis and imaging of a solid tumor of the breast, ovary, cervix, prostate, colon, stomach, kidney, liver, head, neck, lung, blood, pancreas, skin, testicle, thyroid or brain and combinations thereof; most preferentially human prostate cancer cells, that express TF can be performed in accordance with the methods of the invention. A TF antibody or TF antibody fragment of the present invention can also be used for diagnosis in vitro, for example, by using a TF antibody or TF antibody fragment to detect the presence of the cancer marker TF in a fluid sample, such as a tissue sample, plasma, serum, or urine.

TF antibodies and TF antibody fragments can be used in immunoassays to screen body fluids, such as serum, sputum, effusions, urine, cerebrospinal fluid, and the like, for the presence of TF. TF antibodies and TF antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

A TF antibody or antibody fragment, which can include any or all of the antibodies or antibody fragments specific for TF-related gene products, and/or chimeric antibodies or antibody fragments, such as humanized or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. TF antibodies or TF antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present invention includes therapeutic, diagnostic, or therapeutic and diagnostic compositions comprising a TF antibody or TF antibody fragment of the present invention in combination or not with a pharmaceutically acceptable excipient, diluent, or carrier. The present invention also includes a process for preparation of a therapeutic or diagnostic composition comprising admixing an antibody molecule of the present invention together with a pharmaceutically acceptable excipient, diluent, or carrier. An antibody molecule can be the sole active ingredient in the therapeutic or diagnostic composition, or can be accompanied by other active ingredients including other antibody ingredients, for example anti-T cell, anti-TFNγ, or anti-LPS antibodies, or non-antibody ingredients such as xanthines. Compositions can be incorporated into kits for diagnosing or treating diseases characterized by the expression of TF, including, without limitation, solid tumors, and particularly solid tumors of the breast, ovary, cervix, prostate, colon, stomach, kidney, liver, head, neck, lung, pancreas, skin, testicle, thyroid and brain, most preferentially human prostate tumors.

Antibodies or antibody fragments of the present invention are useful for immunoassays which detect or quantitate a TF form bound preferentially by Alper-TF mAb or cells secreting such a TF in a sample. Such an immunoassay typically comprises incubating a biological sample from a subject with a need therefor, such as a man over 40-years old, in the presence of a detectably labeled antibody of the present invention capable of identifying the tumor antigen, and detecting the labeled antibody which is hound in a sample.

In an aspect of the present invention, the status of prostate cancer in a subject can be based on the relative amount, localization or both of one or more forms of TF, including a TF bound preferentially by Alper-TF mAb, in a blood, serum, plasma, or urine sample from a subject in need thereof as compared to that of a normal healthy age-matched subject. In one aspect, that status of cancer is whether the cancer cells are metastatic tumor cells, non-metastatic tumor cells, in particular from prostate cancer cells.

Examples of confirmatory analysis, assays, tests, such as histological examination of samples, and so forth that can be used to confirm or in combination with those disclosed herein include, without limitation, those set forth in Alper, US Publication No. 200810293162.

In an aspect of the present invention the level, localization, or both of one or more forms of TF is diagnostic or prognostic of a disease or outcome probability.

TF antibodies and TF antibody fragments of the present invention are also useful for immunopathological analysis, such as the differential diagnosis of tumor type and the subclassification of the tumor based on its expression or localization of at least one form of TF, including, without limitation, assessment of metastatic potential, predicted responses to therapy, and overall prognosis.

TF antibodies and TF antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy; (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles, soluble proteins, or glycoproteins. The support can then be washed with suitable buffers followed by treatment with the detectably labeled antibody of the present invention. The solid phase support can then be washed with the buffer a second time to remove unbound antibody. The amount of bound label on the solid support can then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric, or visual means. In an alternate embodiment, the enzyme is used to label a binding partner for the antibody of the invention. Such a binding partner can be an antibody against the constant or variable region of the antibody of the invention, such as a heterologous anti-mouse immunoglobulin antibody. Alternatively, the binding partner can be a non-antibody protein capable of binding to the antibody of the present invention.

By radioactively labeling the antibodies of the present invention, it is possible to detect TF through the use of a radioimmunoassay (RIA). The radioactive isotope can be detected by such means as the use of a gamma counter or a scintillation counter or by autoradiography. Isotopes which are particularly useful for the purpose of the present invention are known in the art.

It is also possible to label the antibodies of the present invention with a fluorescent compound. When the fluorescently labeled antibody is exposed to light of the proper wavelength, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase, and sequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, an immunocytochemical assay, including but not limited to an immunohistochemical or immunofluorescence assay. In an aspect, an avidin-biotin immunoperoxidase staining system can be used, and a kit utilizing this system is also contemplated, although the methods of the present invention can utilize any suitable staining procedures known in the art.

Kits according to the present invention can include frozen or lyophilized antibodies to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for an immunocytochemical evaluation, including but not limited to an immunohistochemical or immunofluorescence assay, of cancers, including cancer of the breast, ovary, cervix, prostate, colon, stomach, kidney, liver, head, neck, lung, blood, pancreas, skin, testicle, thyroid and brain, most preferentially, human breast, ovary, head, neck, brain, and prostate in particular human prostate cancer.

The kits including the reagents necessary for an immunocytochemical analysis, including but not limited to an immunohistochemical or immunofluorescence analysis, can be provided as follows: a) TF antibody or antibody fragment of the present invention, or chimeric or humanized variants thereof, b) blocking reagent (in the feral of for example, goat serum) and secondary antibody (such as, for example, goat anti-mouse antibody); c) detectable marker (such as, for example, immunoperoxidase or alkaline phosphatase); and d) developing reagents. The primary antibody (TF antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound a TF antibody, which can or cannot be labeled, for example with a protein such as biotin), which is in turn being used to detect a specific target (in the context of the present invention, the target is a TF expression product).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabeled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of breast, ovary, cervix, prostate, colon, stomach, kidney, liver, head, neck, lung, blood, pancreas, skin, testicle, thyroid and brain, most preferentially human breast, ovary, head, neck, brain, and prostate, in particular human prostate cancer and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

Pharmaceutical Compositions and Methods of Treatment

Another aspect of the invention provides a composition comprising any of these antibodies, optionally in combination with a pharmaceutically acceptable carrier. In another aspect, an antibody of the present invention is optionally in combination with one or more active agents, drugs, or hormones.

The present invention also provides a method of treating human or animal subjects suffering from or at risk of a cancer that expresses TF, such as cancer of the breast, ovary, cervix, prostate, colon, stomach, kidney, liver, head, neck, lung, blood, pancreas, skin, testicle, thyroid, brain, and prostate, most preferentially human prostate, the method comprising administering to the subject a therapeutically effective amount of an antibody of the present invention or a pharmaceutical composition comprising a therapeutically effective amount of an antibody of the present invention.

The term "subject" as used herein refers to any subject in need of treatment, preferably a human patient or subject.

The term "therapeutically effective amount" as used herein refers to an amount of a therapeutic agent needed to treat, ameliorate, or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also he used to determine the appropriate concentration range and route of administration. Such information can then be used to determine useful doses and routes for administration in humans.

An effective amount for a human subject can depend upon the severity of the disease state; the general health of the subject; the age, weight and gender of the subject; diet; time and frequency of administration; drug combination(s); and reaction sensitivities, and tolerance/response to therapy and can be determined by routine experimentation and is within the judgment of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions can be administered individually to a patient or can be administered in combination with other agents, drugs, or hormones. According to some aspects, antibodies can be conjugated with these agents. A summary of the ways in which the antibodies of the present invention can be used therapeutically includes direct cytotoxicity by the antibody, either mediated by complement or by effector cells, or by conjugation to anti-tumor drugs, toxins, and radionuclides. Antibodies can also be used for ex vivo removal of tumor cells from the circulation or from bone marrow.

Cytotoxic proteins can include, but are not limited to, Ricin-A, *Pseudomonas* toxin, *Diphtheria* toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include $^{212}$Bi, $^{131}$I, $^{186}$Re, and $^{90}$Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours), it can be necessary to give one or more doses per day. Alternatively, if the antibody molecule has a long half life (e.g. 2 to 15 days), it can only be necessary to give a dosage once per day, per week, or even every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers, and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it can take the form of a suspension, solution, or emulsion in an oily or aqueous vehicle and it can contain formulatory agents, such as suspending, preservative, stabilizing, and/or dispersing agents. Alternatively, the antibody molecule can be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

A pharmaceutical composition of this invention can be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal, or rectal routes. Hyposprays can also be used to administer the pharmaceutical compositions of the invention. Therapeutic compositions can be prepared as injectables, either as liquid solutions or suspensions. Solid forms suitable for solution in, or suspension in, liquid vehicles prior to injection can also be prepared.

Direct delivery of the compositions will generally be accomplished by injection, subcutaneously, intraperitoneally, intravenously, or intramuscularly, or delivered to the interstitial space of a tissue. Dosage treatment can be a single dose schedule or a multiple dose schedule.

When a TF antibody or TF antibody fragment composition is to be administered by a route using the gastrointestinal tract, the composition can contain additional agents which protect the antibody from degradation but which release the antibody once it has been absorbed from the gastrointestinal tract. Such additional agents are known to those skilled in the art.

Antibodies of the present invention can also be administered in methods of conducting gene therapy, in order to achieve this, DNA sequences encoding the heavy and light chains of the antibody molecule under the control of appropriate DNA components are introduced into a patient such that the antibody chains are expressed from the DNA sequences and assembled in situ.

TF Expression Products as Drug Development Targets

In addition, the present invention relates to the molecular mechanisms resulting in TF antigens for Alper-TF mAb, such as precursor TF being secreted by cancer cells, such as prostate cancer cells. This expression of TF antigens presents novel drug development targets, and accordingly the present invention also relates to the use of such TF antigens as biomarkers that can be targeted not only by the TF antibodies or antibody fragments of the present invention, but also by various other molecules, such as siRNA, antisense oligonucleotides, vaccines, and chemical compounds.

Methods for developing drugs useful in treating and/or diagnosing diseases characterized by the expression of TF antigens for Alper-TF mAb can include the steps of identifying TF antigens for Alper-TF mAb in a subject having a disease, such as prostate cancer, and utilizing those mechanisms of producing TF antigens for Alper-TF mAb to develop and identify drugs that specifically target those molecular mechanisms.

Once candidate drugs have been developed based on the TF antigens, the TF antigens and TF antibodies and TF antibody fragments of the present invention can be used to aid in screening the various drug candidates, in order to identify those drug candidates that exhibit a desired level of specificity for diseased cells presenting TF expression products.

The following examples are non-limiting illustrative examples.

EXAMPLE 1

Approximately 1 µg of purified Alper-TF mAb was suspended in PBS and applied under reducing conditions (boiled 3 minutes in sample buffer with beta-mercaptoethanol and 10% SDS) to 10% Bis-Tris gel. The gel was run at 120 volts, and then stained with Coomassie Blue (0.1% (w/v) Coomassie blue R350, 20% (v/v) methanol, and 10% (v/v) acetic acid), destained in 50% (v/v) methanol in water with 10% (v/v) acetic acid.

Under denatured conditions, the heavy chain of Alper-TF mAb was detected at ~50 ka The light chain of Alper-TF mAb was detected at 25 kDa.

EXAMPLE 2

20 µl of sample buffer containing 50 µg of purified TF and purified TF that was serially diluted 1:1, 1:10, 1:20, or 1:30 (v:v) in sample buffer were boiled 90° C. for 3 minutes and loaded into an 8% Tris-Glycine gel, along with 15 µl of molecular markers. The gel was run at 125V for 1.5 hours. The gel was then transferred to a PVDF membrane. The membrane was incubated with Alper-TF mAb at 4° C. overnight. Subsequently, the membrane was rinsed 3 times for 10 minutes in TBST, incubated with secondary antibody (Sheep anti-mouse IgG-HRP, [Cat # Na931V Lot #352104, GE Healthcare] 1:1,000 diluted in 2% NFDM in TBST) for one hour, rinsed 3 times for 10 minutes in TBST, treated with ECL, and exposed to x-ray film.

The experiment was repeated at least three times, and FIGS. 1A, 1B, and 1C are representative images. FIG. 1A is a Commassie Blue staining of the gel showing a single band at about 77 kDa. FIG. 1B shows one representative image of the results of the Western Blot using Alper-TF mAb. FIG. 1C shows another representative image of the results of the Western Blot using Alper-TF mAb. Alper-TF mAb recognizes a 77 KDa protein (TF).

EXAMPLE 3

Figure 2A:
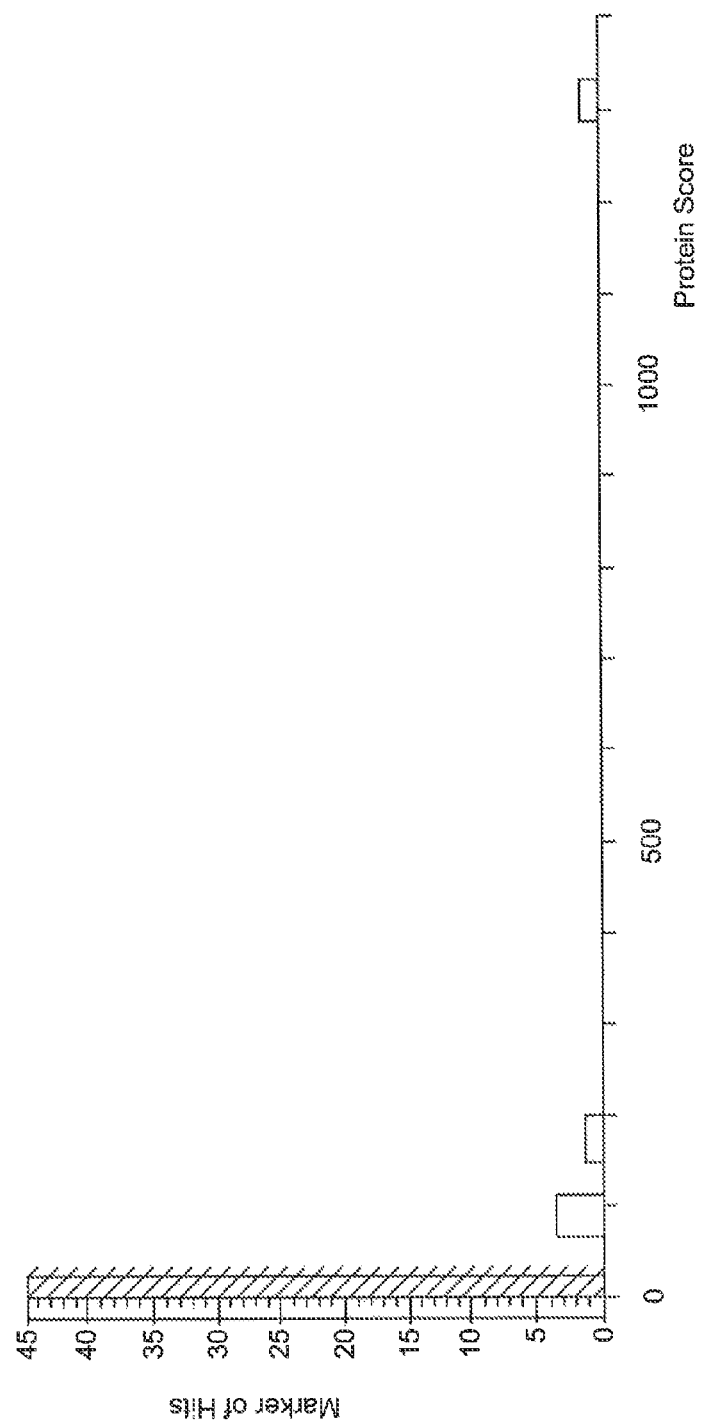
FIG. 2A depicts the ions score of a Mascot protein database search conducted using mass spectrometry data generated from the antigen hound by Alper-TF mAb in graphical form, where a score >34 indicates identity or extensive homology.

The antigen for Alper-TF mAb was isolated, digested with trypsin, and analyzed by MALDI-MS. The Mascot protein database was searched using the mass spectrometry data. The search identified the antigen as corresponding to the human serotransferrin protein (SwissProt TRFE_HUMAN, P02787-1), identifying correspondence to 58 partial TF sequences contained in the database. Protein scores were derived from an ions score as a non-probabilistic basis for ranking protein hits. Based on the probability based mowse scoring, ions score is $-10*\text{Log}(P)$, where P is the probability that the observed match is a random event. Individual ions scores >34 indicate identity or extensive homology ($p<0.05$). FIG. 2A depicts the ions score graphically. The search also identified an albumin (fragment) and hemoglobin alpha and beta, likely contaminants. FIG. 2B shows the details of the 58 matches identified by this search.

EXAMPLE 4

The protein concentrations of OPCT1 cell culture supernatant were determined using BCA Assay (Smith et. al. Anal, Biochem. 150: 76-85, 1985, and Pierce Chemical Co, Rockford, Ill.). OPCT1 cells were derived from prostate tumor epithelium (TlcN0M0, Gleason 3+3) from patients who received no chemotherapy, no radiotherapy, and no hormone treatment (cells were purchased from Asterand Inc.). The samples were then lyophilized, redissolved to 4 mg/ml in SDS Boiling Buffer, and heated in a boiling water bath for 3 minutes before loading onto an 8% acrylamide slab gel.

Western Blotting Methods: 8% acrylamide slab gel electrophoresis was carried out about 4 hours at 15 mA/gel. After slab gel electrophoresis, the gel was placed in transfer buffer (12.5 mM Tris, pH 8.8, 96 mM Glycine, 20% MeOH) and transferred onto a PVDF membrane overnight at 200 mA and approximately 100 volts/2 gels. The following proteins (Sigma Chemical Co., St. Louis, Mo.) were used as molecular weight standards: myosin (220,000), phosphorylase A (94,000), catalase (60,000), actin (43,000), carbonic anhydrase (29,000) and lysozyme (14,000). The blots were then blocked for two hours in 5% nonfat dry milk (NFDM) in Tween-20 tris buffer saline (TTBS) and rinsed in TTBS. The membrane was incubated in primary antibody (Alper-TF mAb antibody diluted 1:125 in 2% NFDM TTBS) overnight. The membrane was rinsed 3 times for 10 minutes in TTBS, incubated with secondary antibody (Sheep antimouse IgG-HRP, [Cat # Na931V Lot #352104, GE Healthcare] 1:1,000 diluted in 2% NFDM in TTBS) for two hours, rinsed 3 times for 10 minutes in TTBS, treated with ECL, and exposed to x-ray film.

A protein with a 77 kDa MWt was detected in culture supernatant prepared from OCPT1 cells when probed with Alper-TF mAb, demonstrating that the Alper-TF mAb specifically binds to TF from human prostate cancer cells in a Western Blot application.

EXAMPLE 5

Plasma samples from healthy control and prostate cancer patients, as determined by pathology of patient biopsies, were assayed for levels of TF by ELISA using Alper-TF mAb. Plasma samples were diluted with PBS at a ratio of 1:100 and coated onto polysorp ELISA plates (Nalgene NUNC® International, Rochester, N.Y.) at 100 µl/well and incubated at 4° C. overnight. The plasma samples were analyzed in a blinded fashion. Wells were washed with PBS and incubated at room temperature for one hour with blocking buffer (5% BSA in PBS). After washing with PBS, the primary antibody, Alper-TF mAb, was added in dilution buffer (45 µg/ml) (PBS buffer, 1% BSA, 0.01% Tween-20), The wells were washed with PBS/0.03% Tween-20 and incubated at room temperature for one hour with 100 µl/well secondary antibody (HRP-Donkey anti-mouse IgG, Jackson ImmunoReseach, West Grove, Pa.) diluted 1:3000. After washing the wells, 100 µl Immunopure TMB substrate solution (Pierce, Rockford, Ill.) was added. The color reaction was stopped by the addition of 100 µl/well 1N $H_2SO_4$. Analysis was performed with a Multiscan Plus ELISA Reader (Thermo Electron Inc.).

Figure 3A:
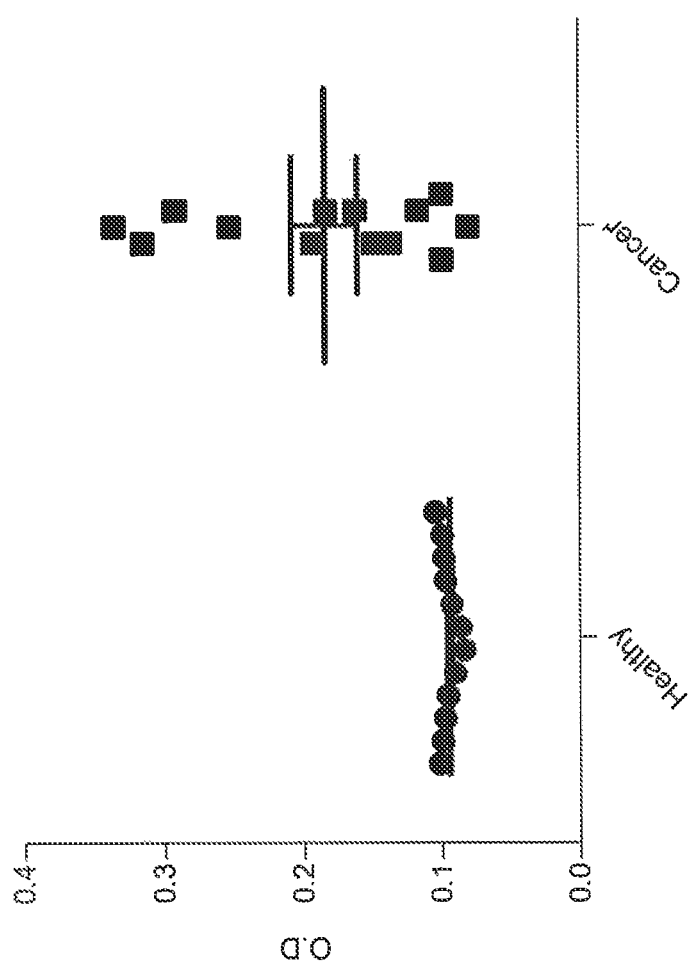
FIG. 3A shows the optical density (OD) values of TF levels in healthy and prostate cancer patients as determined by ELISA.
Figure 3B:
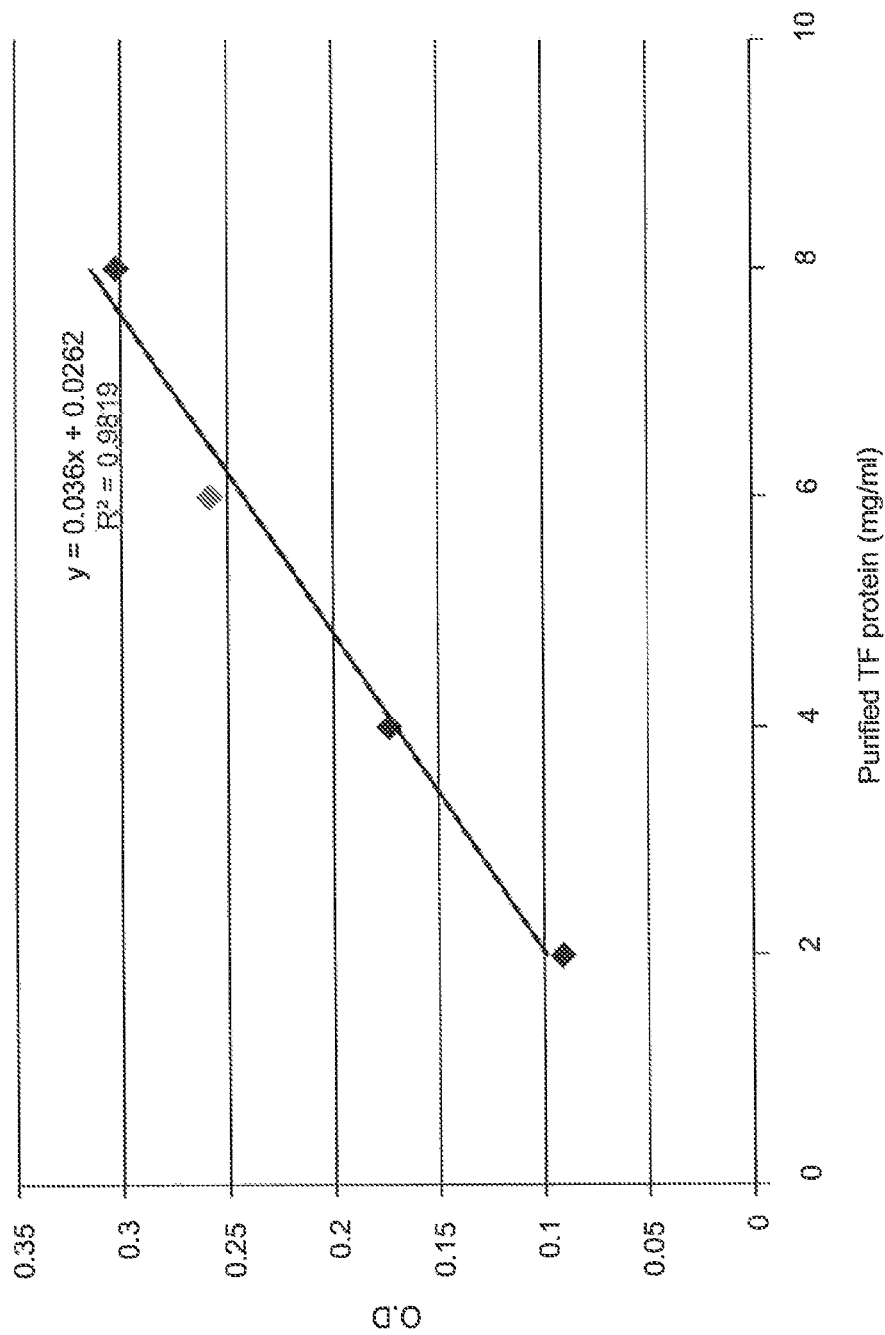
FIG. 3B shows the linear correlation between the concentration of purified TF protein and absorbance values (OD), used as a standard curve in this assay.

FIG. 3A shows the optical density (OD) values of TF levels in healthy and prostate cancer patients. The results show a significant increase in TF levels in cancer patients as compared to healthy controls ($p<0.01$ as determined by unpaired T-test). Alper-TF mAb is useful in immunoassays for the detection of cancer. FIG. 3B shows the linear correlation between the concentration of purified TF protein and absorbance values (OD), used as a standard curve in this assay.

EXAMPLE 6

Figure 4:
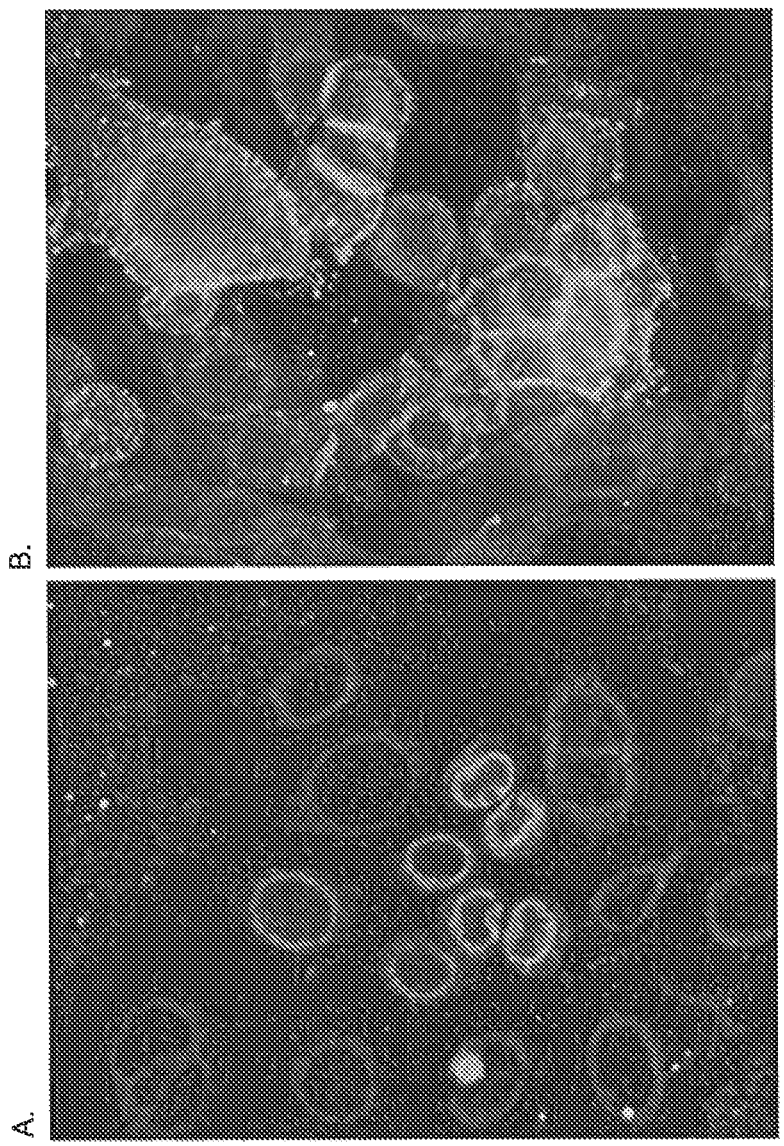
FIG. 4A shows one representative image of the results of an indirect-immunoflourescent staining assay using the Alper-TF mAb with normal prostate cells (OPCN1).
FIG. 4B shows one representative image of the results of an indirect-immunofluorescent staining assay using Alper-TF mAb with early-stage prostate cancer cells (OPCT1).

Normal prostate cells (OPCN1; derived from normal tissue adjacent to cancerous tissue obtained by prostatectomy; available from Asterand Inc.), early-stage prostate cancer cells (OPCT1), and late-stage metastatic prostate cancer cells (LNCaP; available from ATCC, #CRL-1740) were prepared, fixed by incubation with methanol, and incubated overnight with Alper-TF mAb in a standard indirect-immunofluorescent staining assay. See, for example, Ausubel et al., supra FIG. 4A shows one representative image of the results of the indirect-immunofluorescent assay using the Alper-TF mAb with normal prostate cells (OPCN1). FIG. 4B shows one representative image of the results of the indirect-immunofluorescent staining assay using Alper-TF mAb with early-stage prostate cancer cells (OPCT1). Non-cancerous prostate cells show non-punctate staining, whereas early-stage prostate cancer cells show punctuate staining that is typical of localization to early endosomes. Alper-TF mAb is useful in immunocytochemical assays to detect prostate cancer. In one embodiment Alper-TF mAb is useful in immunocytochemical assays for the early detection of prostate cancer.

Figure 5:
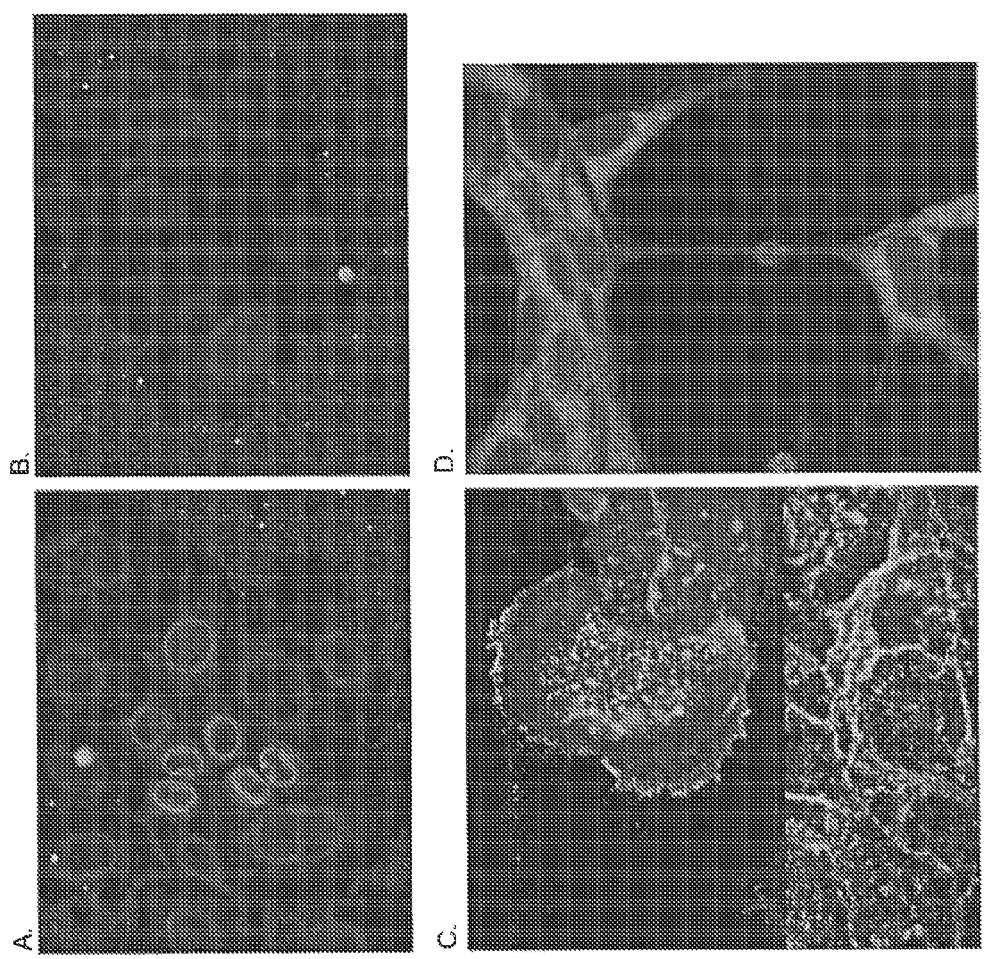
FIGS. 5A and 5B show two representative images of the results of an indirect-immunofluorescent staining assay using the Alper-TF mAb with normal prostate cells (OPCN1 and OPCN2, respectively).
FIG. 5C shows two representative image of the results of an indirect-immunofluorescent staining assay using the Alper-TF mAb with early-stage prostate cancer cells (OPCT1).
FIG. 5D shows one representative image of the results of an indirect- immunofluorescent staining assay using the Alper-TF mAb with late-stage prostate cancer cells (LNCaP).

FIGS. 5A and 5B show two representative images of the results of an indirect-immunofluorescent staining assay using the Alper-TF mAb with normal prostate cells (OPCN1). Staining is non-punctate. FIG. 5C shows two representative image of the results of the indirect-immunofluorescent staining assay using the Alper-TF mAb with early-stage prostate cancer cells (OFCT1). FIG. 5C shows punctate staining typical of localization to early endosomes, and is distinguished from the non-punctate staining shown for non-cancerous prostate cells in FIGS. 5A and 5B.

FIG. 5D shows one representative image of the results of an indirect-immunofluorescent staining assay using the Alper-TF mAb and late-stage prostate cancer cells (LNCaP). FIG. 5D shows non-punctate, diffuse staining that is distinguished from the punctate staining shown for early-stage cancerous prostate cells in FIGS. 5C and 4B, and the non-punctate staining that is shown for the non-cancerous prostate cells of FIG. 4A, FIG. 5A, and FIG. 5B. Alper-TF mAb is useful in immunocytochemical assays to detect prostate cancer. In one embodiment, Alper-TF mAb is useful in immunocytochemical assays for distinguishing early and late stage prostate cancer, and for the early detection of prostate cancer.

EXAMPLE 7

A proprietary nanochip in conjunction with a carbon nanotube field-effect transistor (CNT-FET) platform (available from Fuzbien Technology Institute, Inc) was used to compare Alper-TF mAb binding to TF protein in blood from subjects with early-stage and late-stage prostate cancer to those of blood from healthy, age-matched subjects. The CNT-FET platform detects binding of a ligand, such as binding of an antigen to an antibody, using electronic detectors rather than conventional optical detectors. For each sample, 1 µl of blood was applied to the nanochip. Results indicated significant binding of Alper-TF; mAb to its ligand, TF, in blood from subjects with prostate cancer, as compared to blood from healthy control subjects. There was no increased binding in blood from healthy, age-matched control subjects. In addition, patients with invasive prostate cancer demonstrated increased binding when compared to early-stage prostate cancer patients. Moreover, identification of samples from patients with prostate cancer using Alper-TF mAb was greater and more consistent than binding of commercial antibodies that target PSA and PMSA (currently recognized prostate cancer biomarkers), indicating utilization of Alper-TF mAb to detect TF as a prostate cancer biomarker is superior to detection of PSA.

EXAMPLE 8

OPCT1 cells were cultured on glass-bottomed wells for 18 hours. The cells were permeabilized with Triton X-100.

Transferrin from human serum conjugated to Texas Red (TxR-TF; Molecular Probes, Invitrogen) was added to the culture medium and incubated for 10 minutes. Cells were washed and fixed with 10% paraformaldehyde diluted in PBS for 15 minutes. Cells were again washed with PBS and subsequently incubated with Alper-TF mAb (5 µg/ml) for 15 minutes. Cells were again washed with PBS and subsequently incubated with FITC-conjugated mouse IgG (4 µg/ml) for 15 minutes. Cells were then visualized using an immunofluorescence microscope.

FIG. 11A shows a representative image of the results of the direct immunofluorescence assay for TxR-TF. As expected, TxR-TF, a known endosomal marker, was incorporated into the endosomes during the 10-minute incubation, as demonstrated by the punctate staining. FIG. 11B shows a representative image of the results of the indirect immunofluorescence assay for FITC-labled Alper-TF mAb. Alper-TF mAb fluorescence co-localized with all TxR-TF fluorescence in a similar punctate manner. This image confirms that Alper-TF mAb specifically binds TF, including exogenous TxR-TF localized to the endosomes.

What is claimed is:

1. An isolated antibody that binds serotransferrin (TF), comprising a heavy chain variable domain comprising three complementarity determining regions (CDRs) comprising the amino acid sequences of SEQ ID NO: 2, SEQ ID NO:3, and SEQ ID NO:4 and a light chain variable domain comprising three CDRs comprising the amino acid sequences of SEQ ID NO: 6, SEQ ID NO:7, and SEQ ID NO:8.

2. The isolated antibody of claim 1, comprising a heavy chain variable domain comprising the amino acids of SEQ ID NO:1 and a light chain variable domain comprising the amino acids of SEQ ID NO:5.

3. The isolated antibody of claim 1, wherein TF is a soluble protein having a molecular weight of about 77 kilodaltons as measured by gradient polyacrylamide gel electrophoresis.

4. The isolated antibody of claim 1, wherein said antibody is capable of binding to a precursor or mature for of TF with a specific affinity of between $10^{-8}$ M and $10^{-11}$ M.

5. The isolated antibody of claim 1, wherein said antibody recognizes at least one epitope selected from the group consisting of the amino acids of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:25, or fragments of these amino acids.

6. The isolated antibody of claim 1, immobilized on a solid phase.

7. A pharmaceutical composition comprising the antibody according to claim 1 in combination with a pharmaceutically acceptable carrier.

\* \* \* \* \*